(12) United States Patent
Huang et al.

(10) Patent No.: US 11,925,789 B2
(45) Date of Patent: Mar. 12, 2024

(54) ELASTIC PHYSIOLOGICAL PATCH

(71) Applicant: BIONIME CORPORATION, Taichung (TW)

(72) Inventors: Chun-Mu Huang, Taichung (TW); Chieh-Hsing Chen, Taichung (TW); Jia-Nan Shen, Taichung (TW); Kuan-Lin Chang, Taichung (TW)

(73) Assignee: Bionime Corporation, Taichung (TW)

( * ) Notice: Subject to any disclaimer, the term of this patent is extended or adjusted under 35 U.S.C. 154(b) by 0 days.

(21) Appl. No.: 17/576,536

(22) Filed: Jan. 14, 2022

(65) Prior Publication Data

US 2022/0134002 A1 May 5, 2022

Related U.S. Application Data

(63) Continuation of application No. 16/519,622, filed on Jul. 23, 2019, now Pat. No. 11,426,517.

(30) Foreign Application Priority Data

Jul. 27, 2018 (TW) .................................. 107125993

(51) Int. Cl.
*A61M 5/172* (2006.01)
*A61B 5/00* (2006.01)
(Continued)

(52) U.S. Cl.
CPC ......... *A61M 5/1723* (2013.01); *A61B 5/0031* (2013.01); *A61B 5/6833* (2013.01);
(Continued)

(58) Field of Classification Search
CPC ............ A61M 5/1723; A61M 5/14248; A61M 5/158; A61M 2205/0216;
(Continued)

(56) References Cited

U.S. PATENT DOCUMENTS

| 4,734,092 A * | 3/1988 | Millerd ................. A61M 5/155 604/67 |
| 7,899,511 B2 | 3/2011 | Shults et al. |

(Continued)

FOREIGN PATENT DOCUMENTS

| CN | 1556716 A | 12/2004 |
| CN | 102499663 | 6/2012 |

(Continued)

OTHER PUBLICATIONS

Office Action issued to Japanese counterpart application No. 2019-137304 by the JPO dated Aug. 4, 2020.
(Continued)

*Primary Examiner* — James D Ponton
(74) *Attorney, Agent, or Firm* — Burris Law, PLLC

(57) ABSTRACT

An elastic physiological patch includes a patch assembly and an implant assembly. The patch assembly includes an electronic device, and a soft patch body defining a chamber for receiving the electronic device. The implant assembly is mountable to the electronic device and includes an implant which is capable of being driven to partially pass through the patch body and which is adapted to be implanted in the skin of a subject. The implant and the patch body cooperatively seal the chamber.

20 Claims, 25 Drawing Sheets

(51) Int. Cl.
*A61M 5/142* (2006.01)
*A61M 5/158* (2006.01)

(52) U.S. Cl.
CPC ....... *A61B 5/6849* (2013.01); *A61M 5/14248* (2013.01); *A61M 5/158* (2013.01); *A61M 2205/0216* (2013.01); *A61M 2205/8206* (2013.01); *A61M 2230/201* (2013.01)

(58) Field of Classification Search
CPC .... A61M 2205/8206; A61M 2230/201; A61M 2005/14252; A61M 2205/3317; A61M 2205/3344; A61M 2205/3569; A61M 2205/50; A61B 5/0031; A61B 5/6833; A61B 5/6849; A61B 5/14532; A61B 5/14503
See application file for complete search history.

(56) References Cited

U.S. PATENT DOCUMENTS

| | | | |
|---|---|---|---|
| 9,072,476 | B2 | 7/2015 | Shah et al. |
| 10,028,680 | B2 | 7/2018 | Stafford |
| 2002/0169439 | A1* | 11/2002 | Flaherty ............... A61P 9/10 604/891.1 |
| 2009/0216103 | A1* | 8/2009 | Brister ............... A61B 5/14517 600/347 |
| 2011/0021889 | A1 | 1/2011 | Hoss et al. |
| 2011/0077490 | A1 | 3/2011 | Simpson et al. |
| 2015/0190075 | A1* | 7/2015 | Stafford ............... A61B 5/1451 29/407.1 |
| 2016/0058380 | A1* | 3/2016 | Lee ............... A61B 5/6832 600/365 |
| 2016/0287177 | A1* | 10/2016 | Huppert ............... A61B 5/486 |
| 2017/0290535 | A1* | 10/2017 | Rao ............... A61B 5/1473 |
| 2018/0193554 | A1 | 7/2018 | Meehan et al. |

FOREIGN PATENT DOCUMENTS

| | | |
|---|---|---|
| CN | 108056778 A | 5/2018 |
| EP | 1695727 | 8/2006 |
| JP | 2004532659 | 10/2004 |
| JP | 2006501878 | 1/2006 |
| JP | 2009508639 | 3/2009 |

OTHER PUBLICATIONS

Search Report appended to an Office Action issued to Taiwanese counterpart application No. 107125993 by the TIPO dated Apr. 25, 2019, with an English translation thereof.
Search Report issued to European counterpart application No. 19187644.0 by the EPO dated Oct. 18, 2019.
Search Report appended to an Office Action, which was issued to Chinese counterpart application No. 201810842814.8 by the CNIPA dated Nov. 23, 2021, with an English translation thereof.
Office Action issued to European counterpart application No. 19187644.0 by the EPO dated Dec. 22, 2021.
Office Action issued to parent U.S. Appl. No. 16/519,622 by the USPTO dated Oct. 14, 2021.

* cited by examiner

ELASTIC PHYSIOLOGICAL PATCH

CROSS-REFERENCE TO RELATED APPLICATION

This application is a continuation application of U.S. patent application Ser. No. 16/519,622, filed on Jul. 23, 2019, which claims priority to Taiwanese Patent Application No. 107125993, filed on Jul. 27, 2018.

FIELD

The disclosure relates to a patch, more particularly to a physiological patch suitable for use on a human body.

BACKGROUND

Referring to FIGS. 1 and 2, a conventional sensor patch 1, as disclosed in U.S. Pat. No. 7,899,511B2, includes an adhesive pad 11 for adhering to the skin of a user, a base 12 adhered to the adhesive pad 11, a mounting seat 13 disposed in the base 12, a sensor installed on the mounting seat 13, and an electronic device 15 disposed on the base 12 and electrically connected to the sensor 14. However, during use of the conventional sensor patch 1, an external liquid (such as a body liquid) often penetrates into the base 12 through a hole in the adhesive pad 11 or into the mounting seat 13 along the sensor 14, causing damage to the electronic device 15. To avoid this phenomenon, a sealant is coated on a junction between the sensor 14 and the mounting seat 13 and a junction between the mounting seat 13 and the base 12 during assembly, and is then heated to liquefy and penetrate into gaps, thereby achieving a closed waterproof effect. In practice, the sealant may be replaced by an ultrasonic welding or O-ring.

However, the aforementioned waterproof sealing method has its disadvantages. In terms of applying the sealant, it is required to heat the sealant after it is coated on each junction, so that the process is rather cumbersome, and the assembly is more difficult. The ultrasonic welding also has the same cumbersome assembly problem as that of the sealant, and its fusion temperature may damage the electronic device 15. In O-ring, the sealing effect is achieved by pressing two objects tightly against the O-ring, so that the O-ring is more suitable for use in sealing hard objects, such as the base 12 and the mounting seat 13. However, because the physical strength of the sensor 14 is low, a tight pressing force may increase the risk of damage of the sensor 14, so that the O-ring is not suitable for use in sealing the sensor 14.

SUMMARY

Therefore, an object of the present disclosure is to provide an elastic physiological patch that is capable of alleviating at least one of the drawbacks of the prior art.

According to this disclosure, an elastic physiological patch includes a patch assembly and an implant assembly. The patch assembly includes an electronic device, and a soft patch body defining a chamber for receiving the electronic device. The implant assembly is mountable to the electronic device and includes an implant which is capable of being driven to partially pass through the patch body and which is adapted to be implanted in the skin of a subject. The implant and the patch body cooperatively seal the chamber.

BRIEF DESCRIPTION OF THE DRAWINGS

Other features and advantages of the present disclosure will become apparent in the following detailed description of the embodiments with reference to the accompanying drawings, of which.

DETAILED DESCRIPTION

Figure 1:
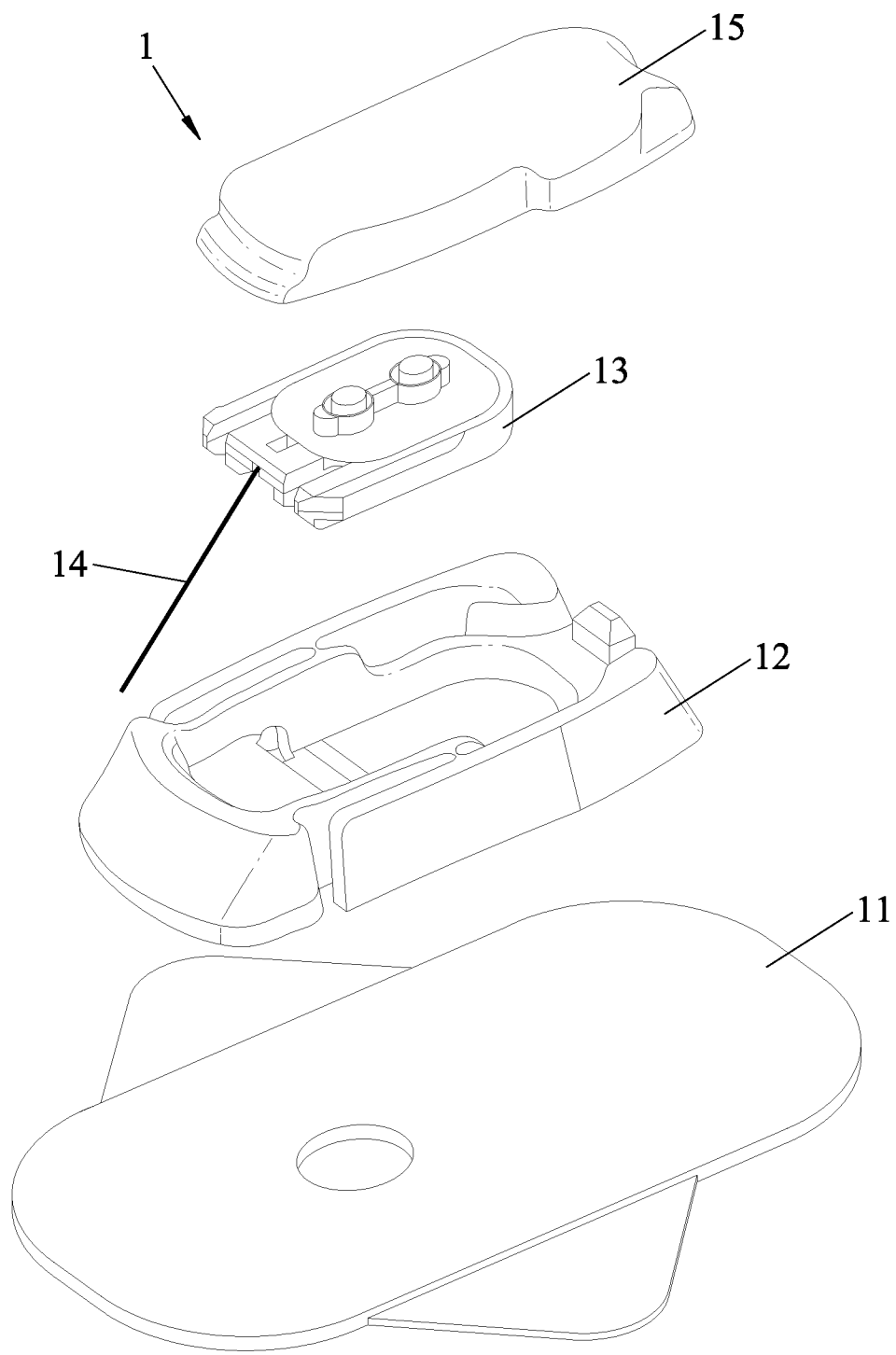
FIG. 1 is an exploded perspective view of a conventional sensor patch disclosed in U.S. Pat. No. 7,899,511B2.
Figure 2:
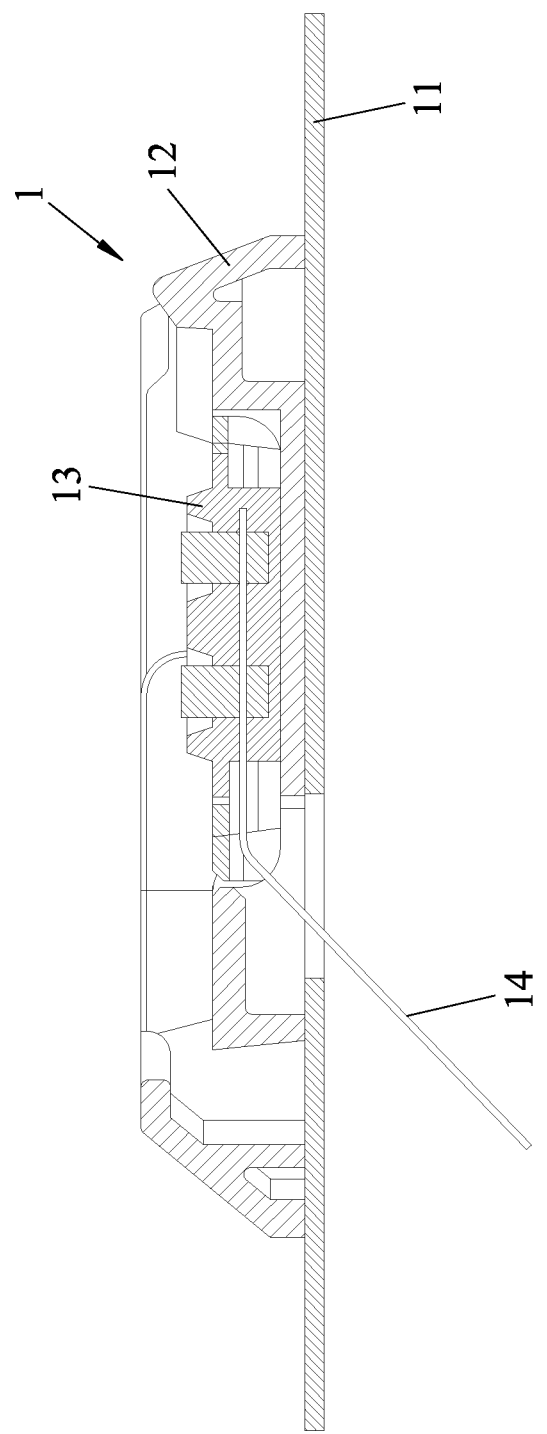
FIG. 2 is an assembled sectional side view of the conventional sensor patch of FIG. 1.
Figure 3:
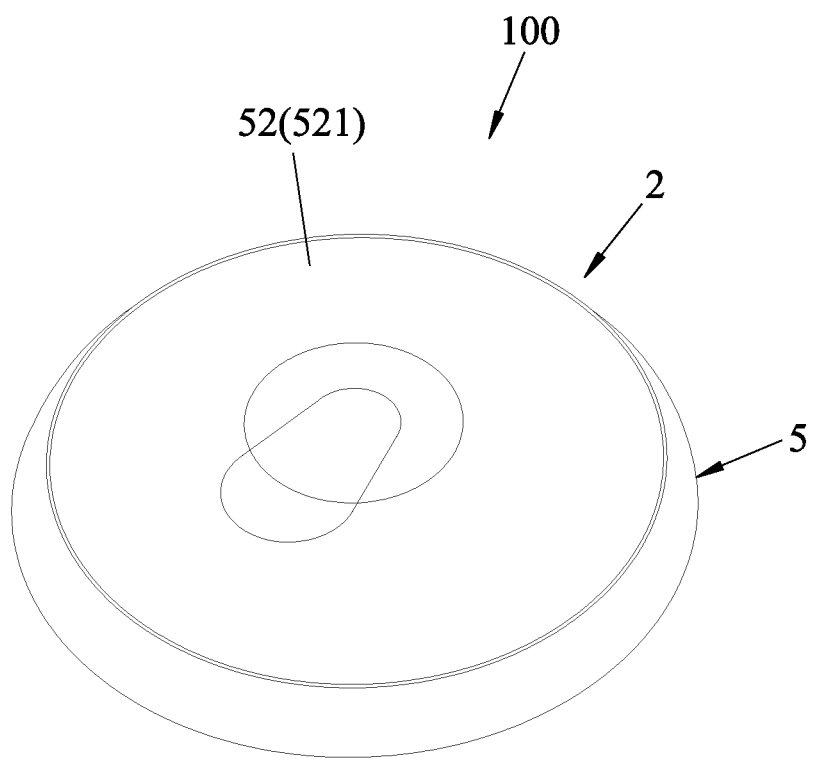
FIG. 3 is a perspective view of an elastic physiological patch according to the first embodiment of the present disclosure.

Before the present disclosure is described in greater detail with reference to the accompanying embodiment, it should be noted herein that like elements are denoted by the same reference numerals throughout the disclosure.

Referring to FIGS. 3 to 6, an elastic physiological patch 100 according to the first embodiment of the present disclosure is suitable to be adhered on the skin of a subject, such as a human body, for use in measuring the glucose level of the human body. The elastic physiological patch 100 includes a patch assembly 2 and an implant assembly 3.

The patch assembly 2 includes an electronic device 4 and a soft patch body 5. The electronic device 4 includes a circuit board 41, a transmitting unit 42, and a battery 43 for supplying power to the transmitting unit 42. The circuit board 41 has two spaced-apart signal reading areas 411 for receiving signals, and a through hole 412. The circuit board 41 may be made of a soft or hard board. In order to obtain a better mechanical strength, the circuit board 41 of this embodiment is made of a hard board.

The transmitting unit 42 is disposed on the circuit board 41 for receiving electrical signals from the signal reading areas 411 and outputting a corresponding glucose level signal. The transmitting unit 42 includes a signal amplifier 421, an analog digital signal converter 422, a processor 423 and a transmitter 424 interconnected to one another. The signal amplifier 421 is used for receiving and amplifying the electrical signals. The analog digital signal converter 422 converts the amplified electrical signals into a corresponding digital signal. The processor 423 converts the corresponding digital signal into a glucose level signal. The transmitter 424 is used for transmitting the glucose level signal to an external receiving device 91. Those skilled in the art may adjust the internal configuration of the transmitting unit 42 according to the requirement, and is not limited to what is disclosed herein.

Figure 4:
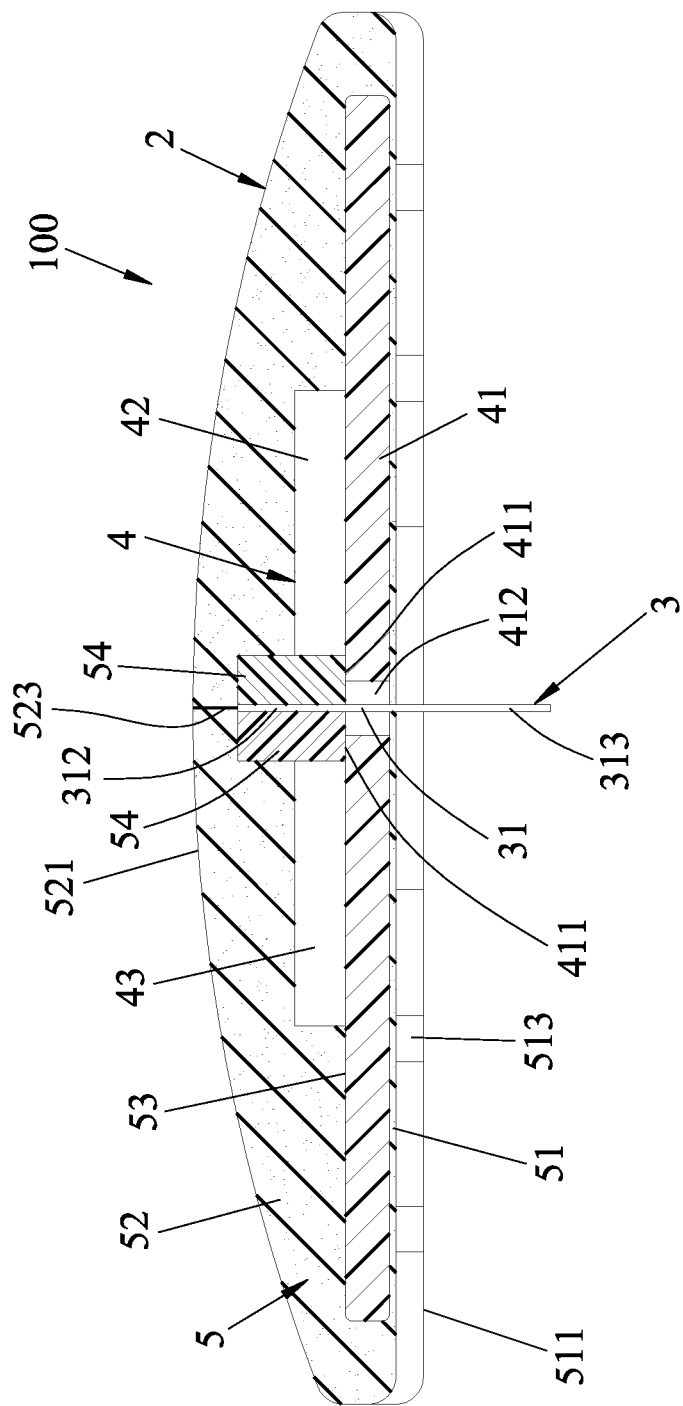
FIG. 4 is a front sectional view of the first embodiment.
Figure 5:
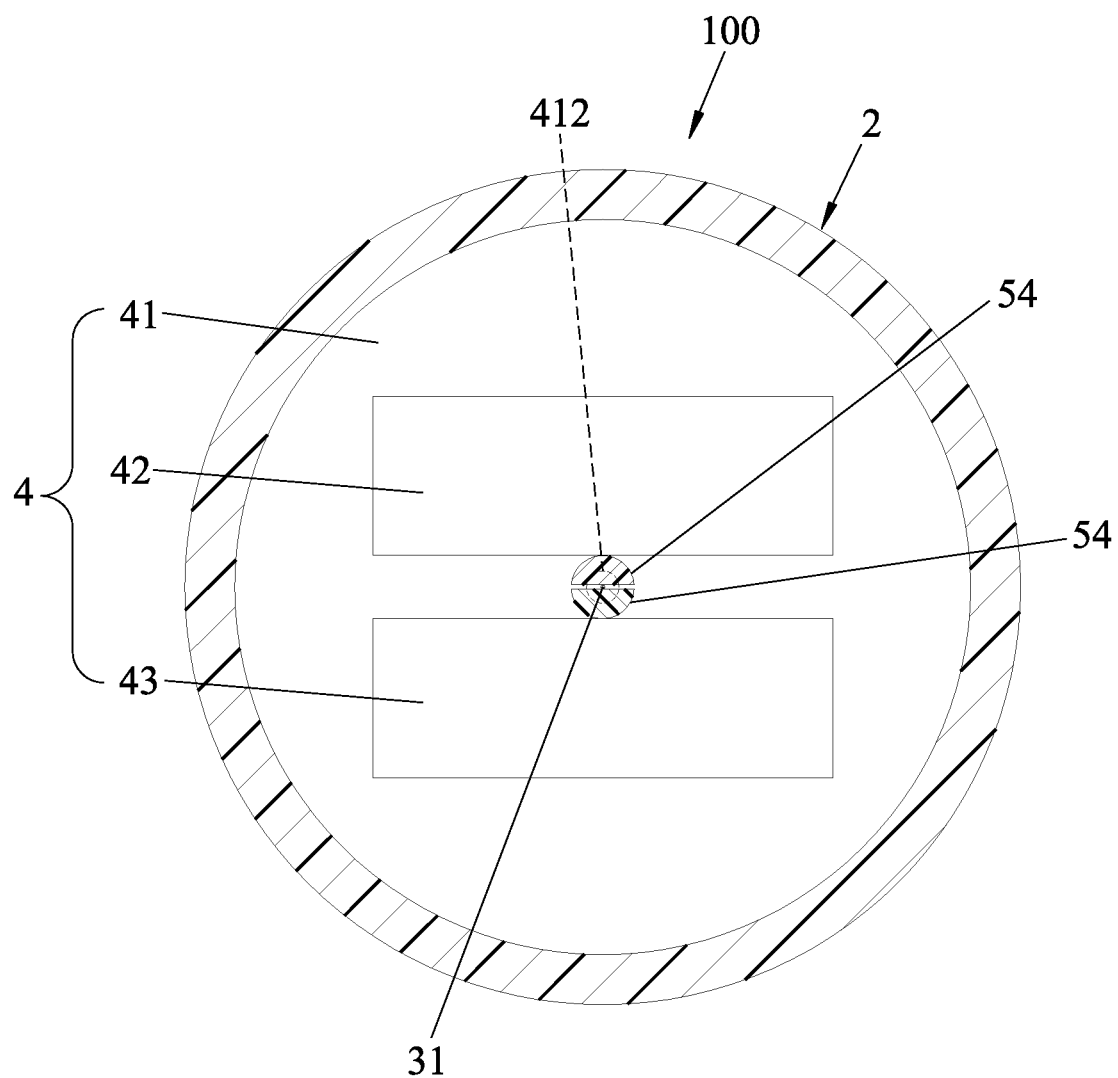
FIG. 5 is a top sectional view of the first embodiment.
Figure 6:
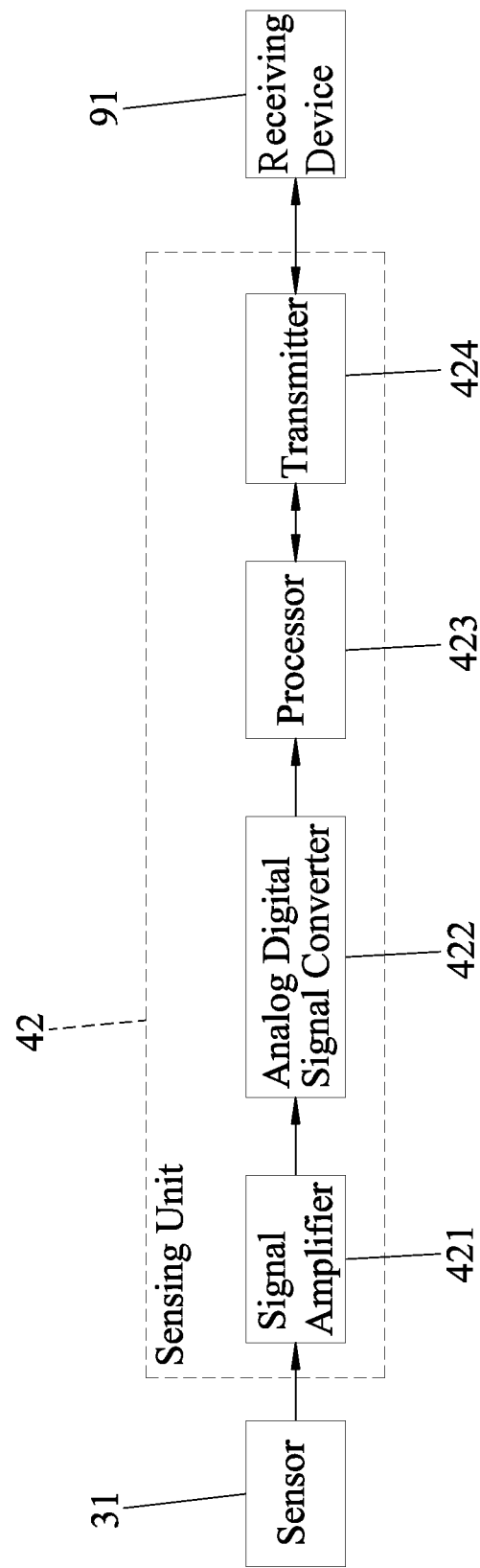
FIG. 6 is a block diagram of a transmitting unit of the first embodiment.
Figure 7:
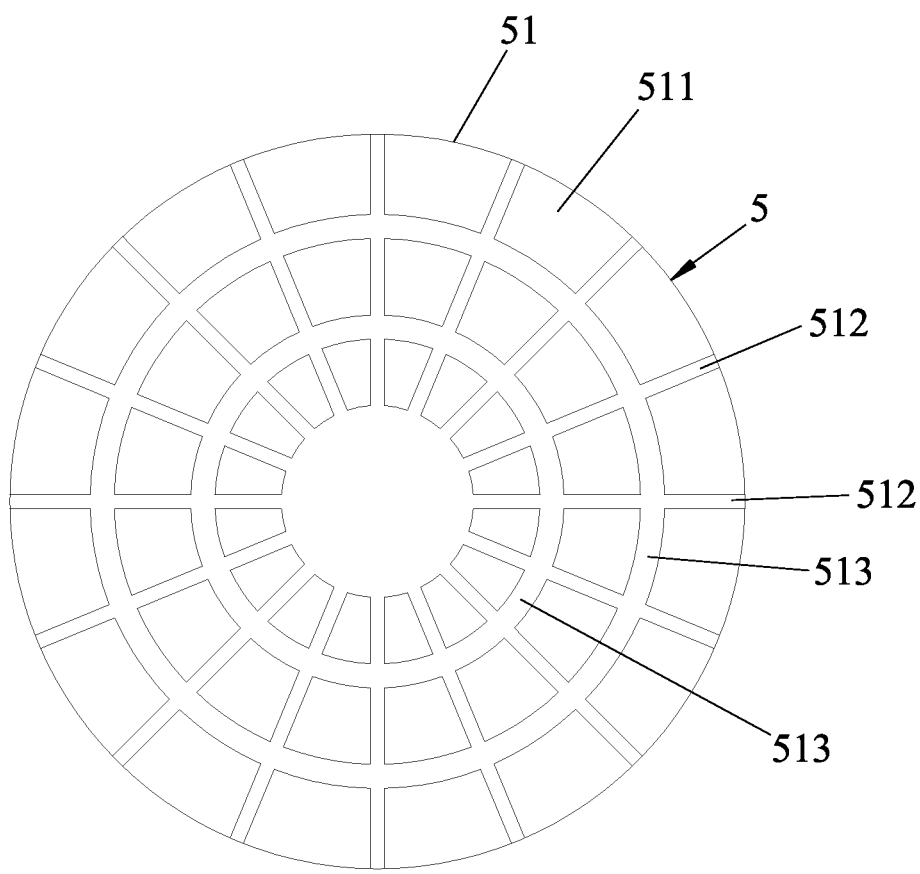
FIG. 7 is a bottom view of a patch body of the first embodiment.

Referring to FIG. 7, in combination with FIG. 4, the patch body 5 covers the electronic device 4, has a disk shape, and is made of thermosetting or thermoplastic elastomer. The elastomer has an inject-ion temperature ranging from 140 to 170° C. Preferably, the elastomer is selected from a group consisting of silica gel, silicone, polyurethane (PU), and a combination thereof. The patch body 5 has a bottom wall 51, a top wall 52 opposite and connected to the bottom wall 51 and cooperating with the same to define therebetween a chamber 53 for receiving the electronic device 4, and two spaced-apart electrical connection pieces 54. The top wall 52 has a curved top surface 521. The bottom wall 51 is circular, and has an adhering surface 511 for being adhered to the skin of the human body, and a plurality of long-strip grooves 512 and a plurality of ring-shaped grooves 513 formed in the adhering surface 511. The long-strip grooves 512 are radially extending grooves. The ring-shaped grooves 513 are arranged concentrically. The electrical connection pieces 54 are disposed in the chamber 53, and each electrical connection piece 54 contains a conductive material for electrical connection with a respective one of the signal reading areas 411 of the circuit board 41.

To make the patch assembly 2, the electronic device 4 is first placed in a mold (not shown), after which the signal reading areas 411 of the circuit board 41 are injected with conductive silicone to use as the electrical connection pieces 54 of the patch body 5, followed by injection of silicone to completely cover the electronic device 4. Another way of making the patch assembly 2 is to weld two metal elastic pieces to the respective signal reading areas 411 firstly, after which the electronic device 4 is placed in the mold, followed by injection of silicone to completely cover the electronic device 4. Portions of the metal elastic pieces are exposed from the silicone for electrical connection with the implant assembly 3. The metal elastic pieces may be replaced by silicone conductive strips. The making of the patch assembly 2, apart from the foregoing methods, may also use other manufacturing methods, as long as the patch body 5 can integrally and completely encapsulate the electronic device 4, any method is acceptable.

Figure 8:
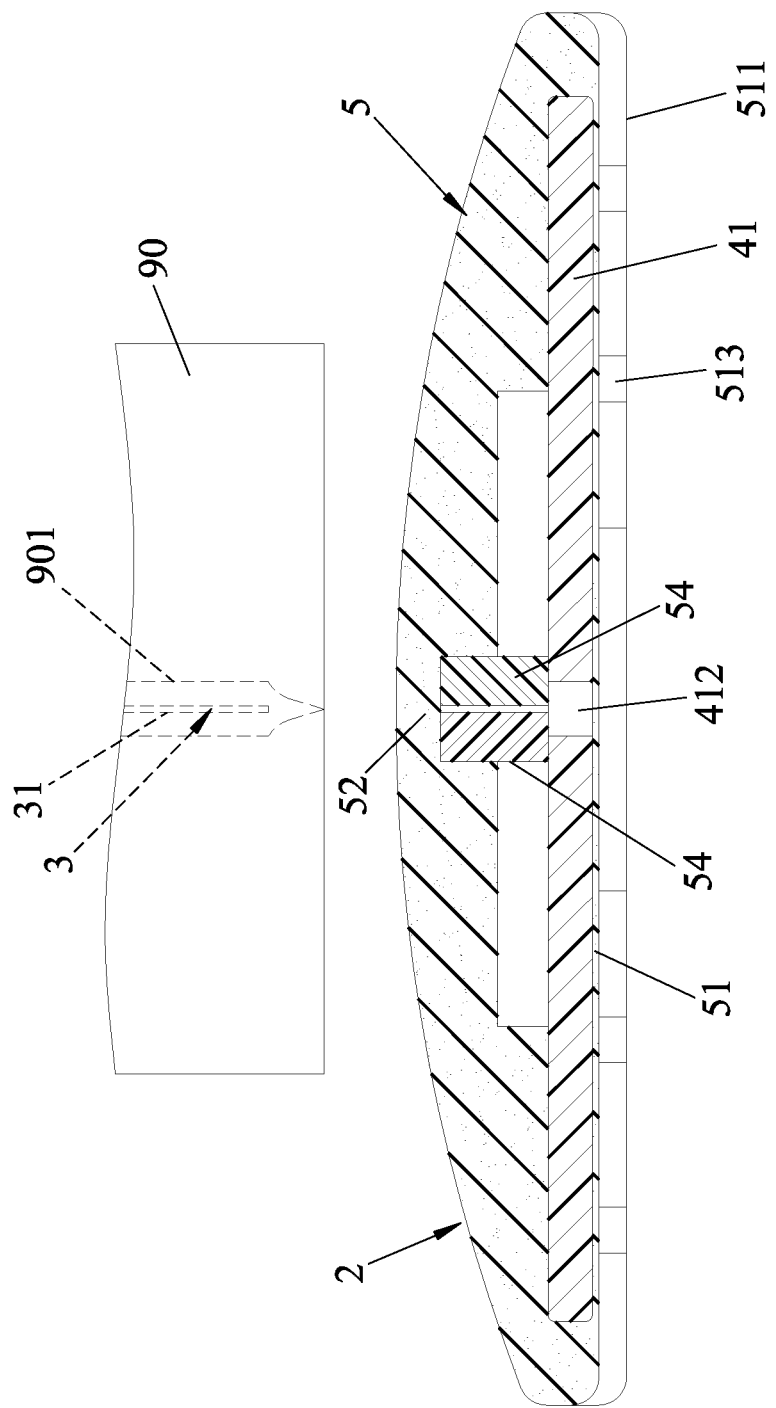
FIG. 8 is another front sectional view of the first embodiment, illustrating how an implant assembly of the first embodiment is disposed in a guide needle of an insertion device and is aligned with a patch assembly of the first embodiment.
Figure 9:
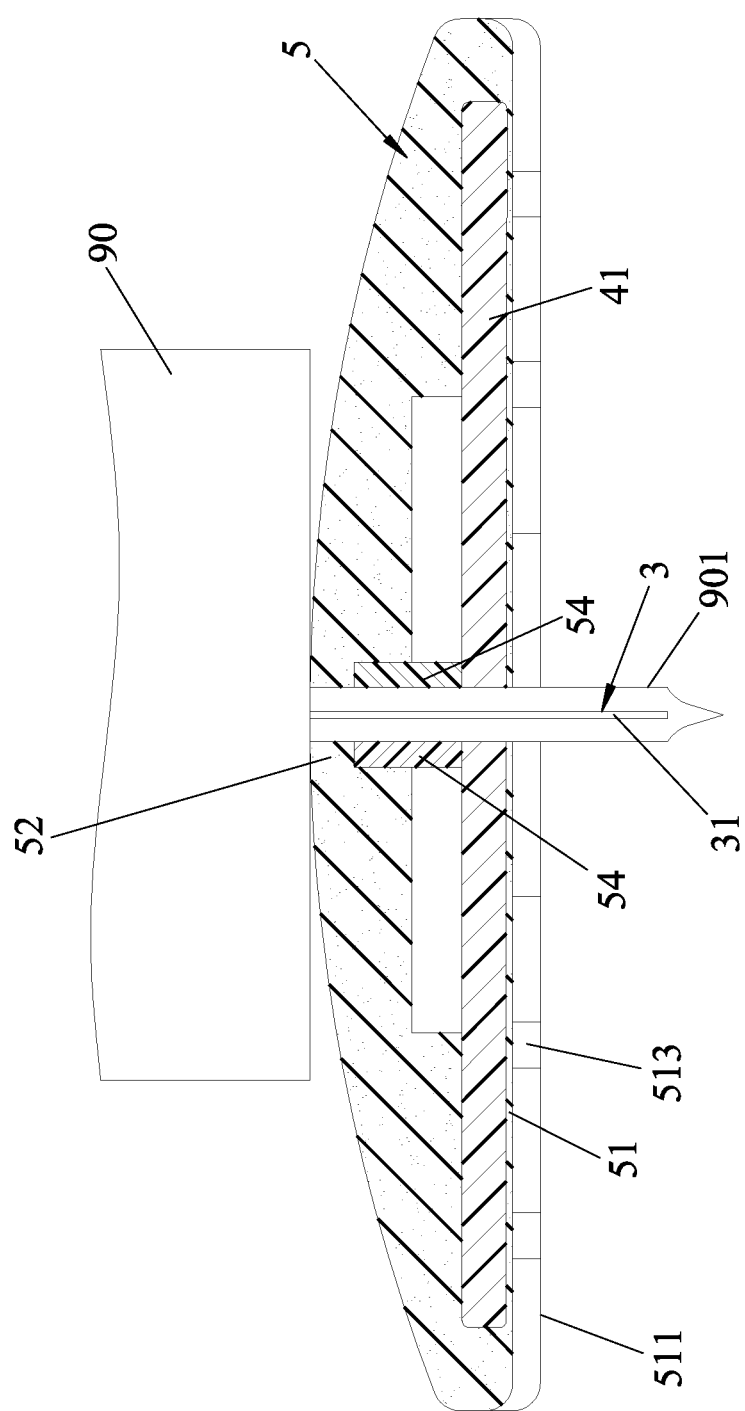
FIG. 9 is a view similar to FIG. 8, but with the guide needle together with the implant assembly extending through the patch assembly.

Referring to FIGS. 8 and 9, in combination with FIG. 4, to use the elastic physiological patch 100, the patch assembly 2 is first placed on the skin of a human body, after which the implant assembly 3 is mounted to the patch assembly 2 and is connected to the electrical connection pieces 54 of the patch body 5 to electrically connect with the electronic device 4. The implant assembly 3 includes an implant 31. In this embodiment, the implant 31 is a sensor for measuring glucose level. The implant or sensor has a signal output end 312 and a sensing end 313. The sensor 31 is linear, and has two sides each of which is provided with an electrode for electrical connection with the respective electrical connection piece 54.

In this embodiment, a mounting method of the implant assembly 3 is to detachably position the sensor 31 firstly into a hollow guide needle 901 of an insertion device 90 that is disposed on an outer side of the patch assembly 2, after which the guide needle 901 is aligned with the through hole 412 (see FIG. 8) in the circuit board 41, followed by the triggering of the guide needle 901, so that the guide needle 901 together with the sensor 31 is driven to pass in sequence from the outer side of the patch assembly 2 through the top wall 52 of the patch body 5, between the electrical connection pieces 54, the through hole 412 and the bottom wall 51 (see FIG. 9), and into the skin of the human body. Afterwards, the guide needle 901 is withdrawn by the insertion device 90 for leaving the signal output end 312 of the sensor 31 fixed by the patch assembly 2 and the sensing end 313 of the sensor 31 implanted in the skin of the human body, as shown in FIG. 4.

Figure 10:
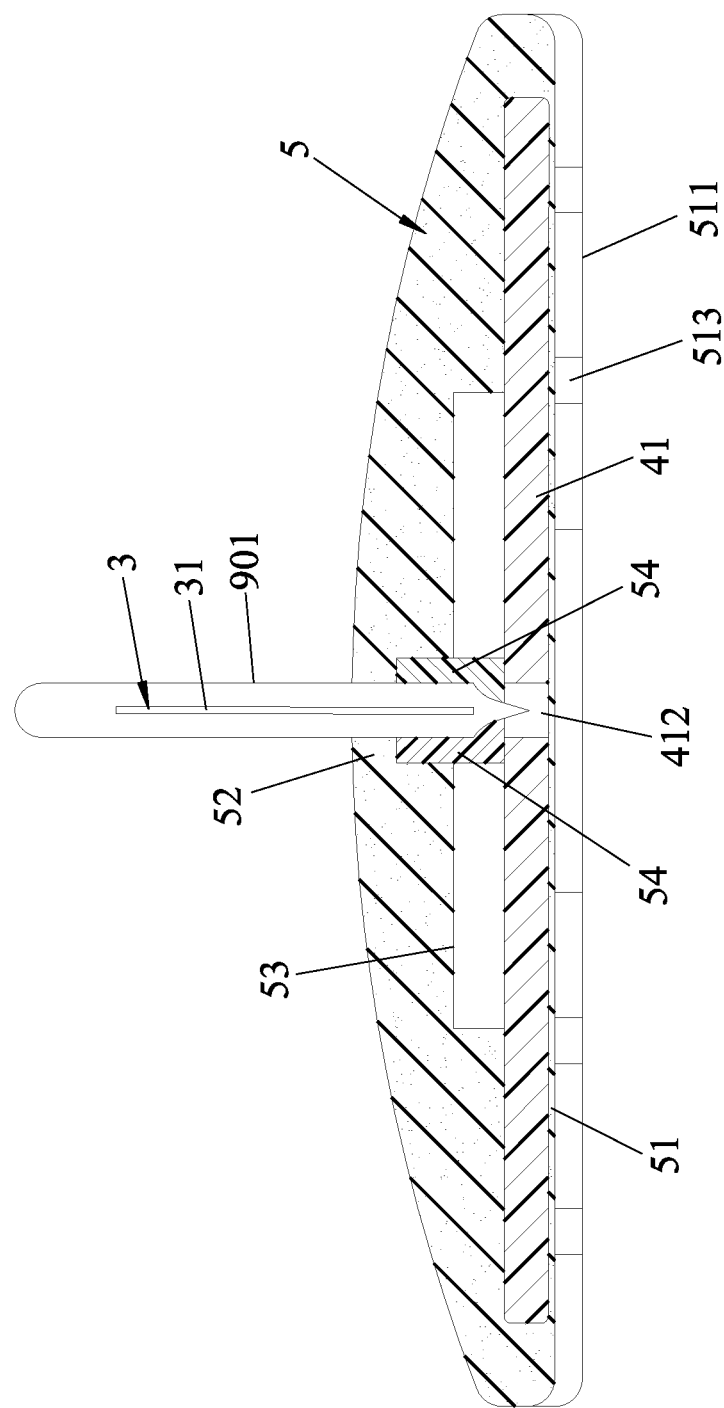
FIG. 10 illustrates how the guide needle together with the implant assembly is disposed in the patch assembly.

Referring to FIG. 10, in combination with FIG. 4, another mounting method of the implant assembly 3 is to combine the sensor 31 with the guide needle 901 firstly, after which they are directly inserted into the chamber 53 of the patch assembly 2. To attach the elastic physiological patch 100 to the human body, the patch assembly 2 is first adhered to the skin of the human body, after which the guide needle 901 together with the sensor 31 is driven to pierce through the bottom wall 51 of the patch body 5 into the human body through the insertion device (see FIG. 9), and then the guide needle 901 is pulled out by the insertion device 90 for leaving the sensor 31 implanted in the skin of the human body. Generally, the insertion device 90 includes an implant holder (not shown) and a guide needle holder (not shown). When the implant holder is pressed downward, because there is a corresponding structure inside the implant holder for covering the guide needle holder, the guide needle holder can move along with the implant holder, and then withdraw the guide needle leaving the implant in the skin of the human body. Since the implant holder and the guide needle holder are two independent components, and since only the guide needle holder is provided with a return spring for returning the guide needle holder to its original position, only the guide needle connected to the guide needle holder can be withdrawn leaving the implant in the skin of the human body. For details of the structure and operation of the insertion device, reference may be referred to U.S. Patent Application Publication No. 2017/0290533A1. Since the insertion device 90 is known in the art, the present disclosure is not limited to the above-mentioned example and only illustrates the guide needle 901 and the sensor 31 disposed in the guide needle 901 in FIG. 10. It is worth to mention herein that the implant operation may not use the insertion device 90, and may be done manually, as long as the guide needle 901 can be inserted and pulled out to similarly achieve the implantation of the sensor 31.

Since the patch body 5 is integrally formed and encapsulates the electronic device 4, the electronic device 4 can be well protected. Further, by virtue of the material characteristics of the patch body 5, when the guide needle 901 pierces through and is withdrawn from the top wall 52 of the patch body 5, the patch body 5 will rebound and extrude a passage 523 pierced by the guide needle 901 to achieve sealing and waterproof effects; and when the guide needle 901 pierces through and is withdrawn from the bottom wall 51 of the patch body 5, the patch body 5 will rebound and tightly hold the implant 31 and will cooperate with the implant 31 to seal the chamber 53. That is, apart from the portion pierced by the guide needle 901, the patch body 5 does not have any other hole, so that it has an excellent isolating effect. It is worth to mention herein that to take into account a tight sealing effect between the implant 31 and the bottom wall 51 of the patch body 5 and a mounting resistance needed to overcome when the guide needle 901 together with the implant or sensor 31 pass through the patch body 5, the thickness of the bottom wall 51 is ranged from 0.2 mm to 1 mm. Preferably, the thickness of the bottom wall 51 is ranged from 0.2 mm to 0.5 mm to ensure that the guide needle 901 together with the sensor 31 can smoothly pass through the bottom wall 51 and the sensor 31 can have a sufficient contact area with the bottom wall 51 when the guide needle 901 is withdrawn so as to block moisture from entering the chamber 53, thereby achieving an effective waterproof.

From the foregoing, the advantages of this disclosure can be summarized as follows:

1. When the implant or sensor 31 of the implant assembly 3 is disposed in the patch assembly 2, the assembly of the physiological patch 100 is completed and is convenient. Moreover, because the patch body 5 can completely cover or encapsulate the electronic device 4 and can tightly hold the implant 31, the patch body 5 can cooperate with the implant 31 to achieve sealing and waterproof effects of the physiological patch 100.

2. The making of the patch assembly 2 is easy. Just by injecting soft material into a mold to cover the electronic device 4 and followed by solidification, the making of the patch assembly 2 is completed. Further, the electrical connection pieces 54 can be formed on the respective signal reading areas 411 of the electronic device 4 by simply pouring adhesive in batches, so that there is no need for additional provision of conductive components. Hence, the manufacturing cost can be reduced.

3. The material of the patch body 5 is selected from elastomers having an injection temperature ranging from 140 to 170° C. This temperature range can ensure that the electronic device 4 encapsulated by the patch body 5 will not be damaged.

4. The patch body 5 is made of a soft material, so that it can follow the bends and curves of the skin of the human body so as to adhere closely to the skin, thereby reducing the possibility of removal therefrom.

5. When the patch body 5 is adhered to the skin of the human body, the long-strip grooves 512 and the ring-shaped grooves 513 thereof can increase permeability, thereby reducing the possibility of skin allergies.

Referring to FIGS. 11A to 11C and 12A to 12C, the second embodiment of the elastic physiological patch 100' according to this disclosure is generally identical to the first embodiment, and differs in that, in the second embodiment, the implant assembly 3 is disposed in the chamber 53 and further includes two conductive members 32 and an insertion device 33, and the electronic device 4 further includes a guide member 46 disposed on the circuit board 41. The electrical connection pieces 54 (see FIG. 4) are dispensed herewith.

The conductive members 32 are respectively disposed on the signal reading areas 411.

The insertion device 33 includes a trigger mechanism 331 and a hollow guide needle 332. The trigger mechanism 331 is operable to drive the action of the guide needle 332, and includes a track 333, a movable seat 334, a pivot arm assembly 335, and a torsion spring 336. The movable seat 334 is slidably disposed on the track 333. The guide needle 332 is connected to the movable seat 334. The pivot arm assembly 335 is composed of two pivot arms (337a, 337b) pivoted to each other. The pivot arm (337a) has two opposite ends respectively pivoted to the pivot arm (337b) and the movable seat 334. The pivot arm (337b) has two opposite ends respectively pivoted to the pivot arm (337a) and the torsion spring 336. The implant or sensor 31 is detachably positioned in the guide needle 332.

Figure 11A:
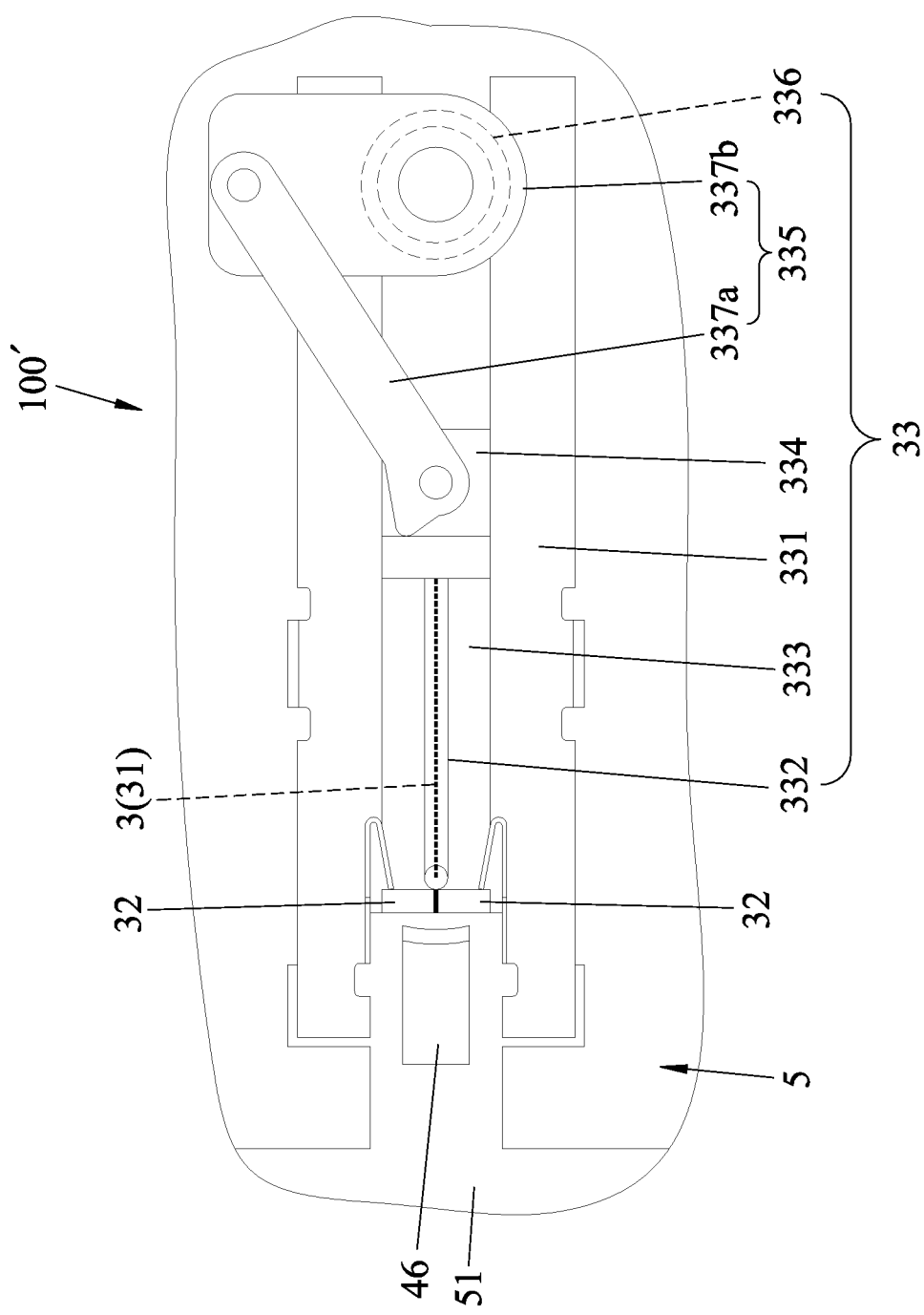
FIG. 11A is a fragmentary top view of an elastic physiological patch according to the second embodiment of the present disclosure, illustrating a trigger mechanism of the implant assembly in a state prior to being triggered.
Figure 11B:
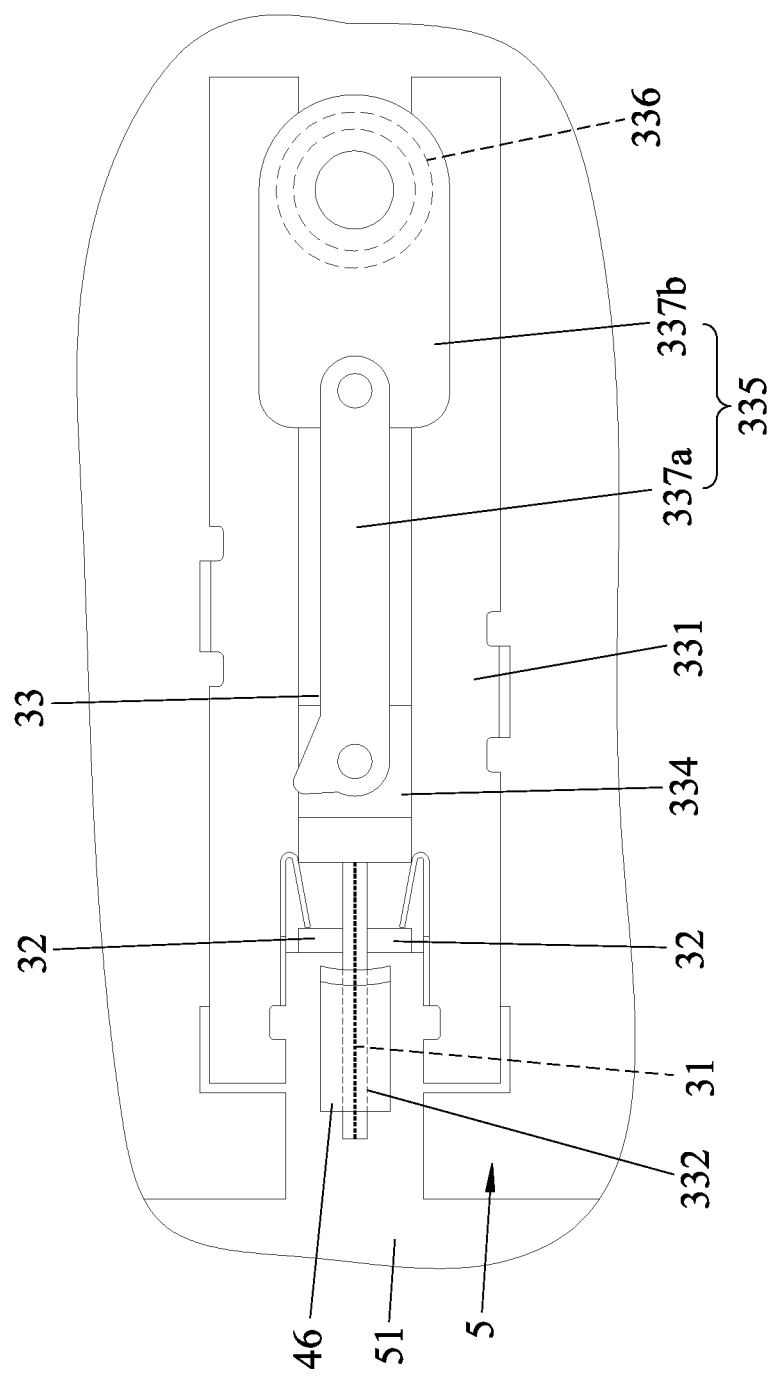
FIG. 11B is a view similar to FIG. 11A, but with the trigger mechanism being triggered to push a guide needle together with an implant disposed in the guide needle.
Figure 11C:
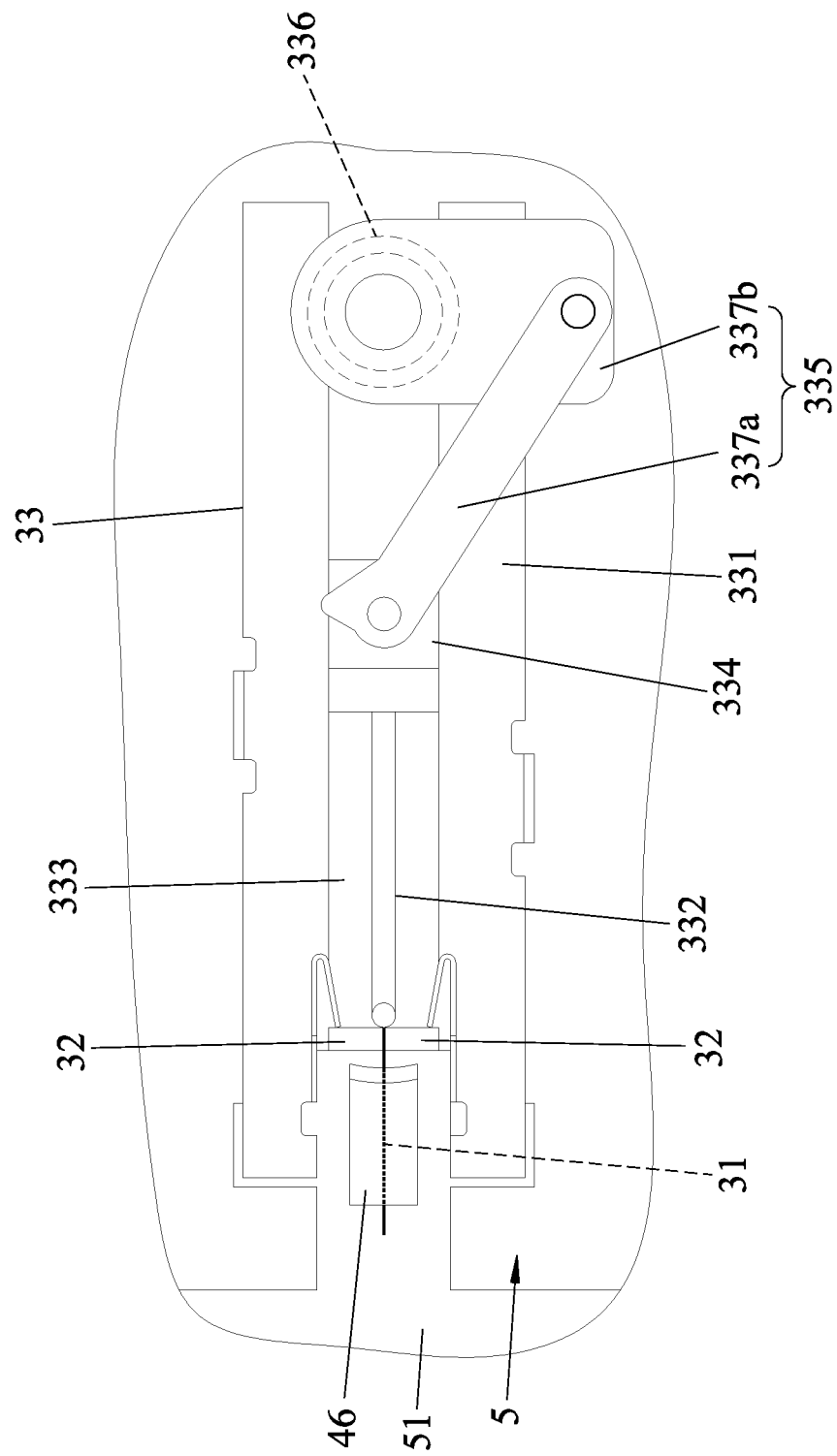
FIG. 11C is a view similar to FIG. 11B, but with the guide needle being retracted leaving the implant.
Figure 12A:
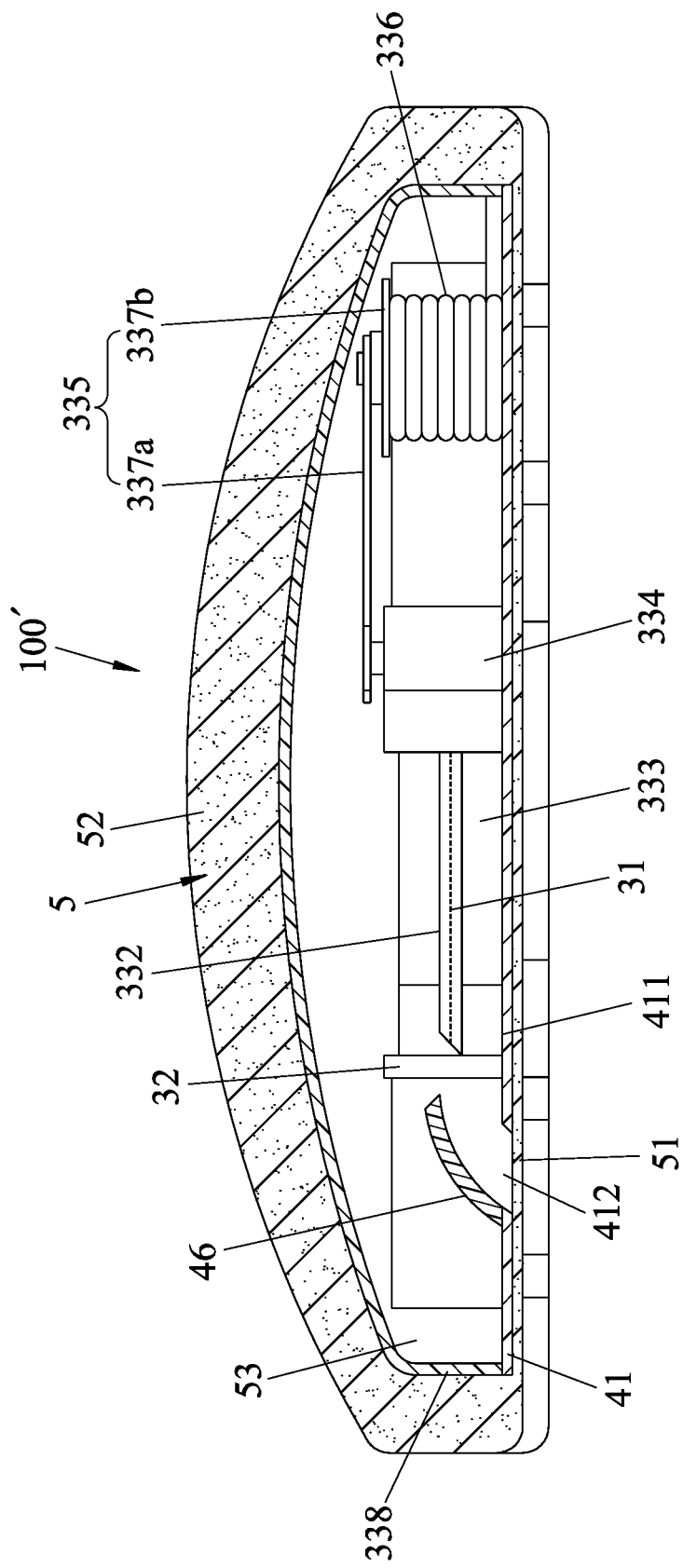
FIG. 12A is a side sectional view of the second embodiment, illustrating the trigger mechanism prior to being triggered.
Figure 12B:
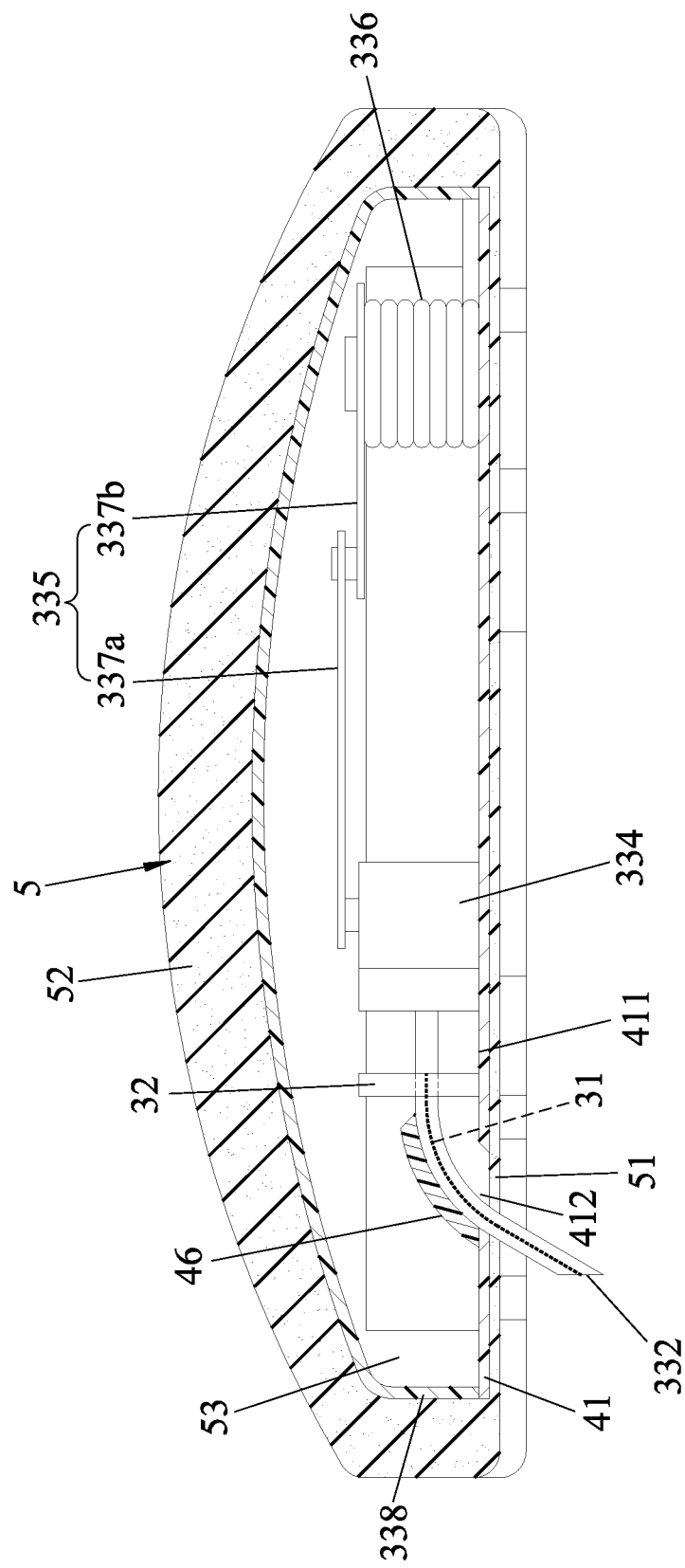
FIG. 12B is a view similar to FIG. 12A, but with the trigger mechanism being triggered to push the guide needle together with the implant.
Figure 12C:
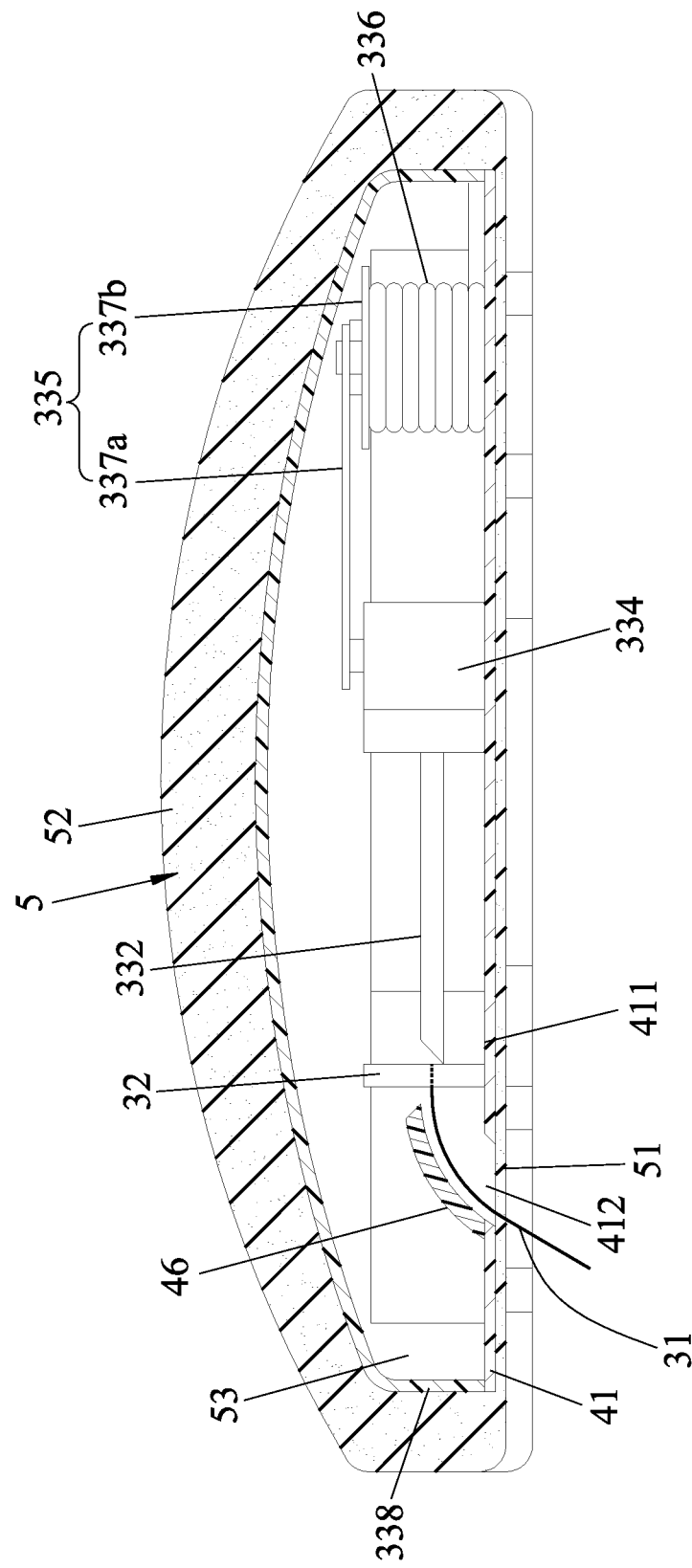
FIG. 12C is a view similar to FIG. 12B, but with the guide needle being retracted leaving the implant.

Prior to activation of the trigger mechanism 331, as shown in FIGS. 11A and 12A, the movable seat 334 is held immovably on the track 333. The track 333 can be limited by any position limiting mechanism. Furthermore, the movable seat 334 is coupled to the pivot arm (337a) so as to be temporarily stopped and then driven by the pivot arm assembly 335 cooperated with the torsion spring 336. As shown in FIGS. 11B and 12B, as the movable seat 334 is released, the torsion spring 336 will rotate to drive the action of the pivot arm assembly 335, which in turn will push the movable seat 334 to move toward the conductive members 32. As the movable seat 334 moves toward the conductive members 32, the guide needle 332 together with the sensor 31 will pass through between the conductive members 32, and is guided by the guide member 46 to move toward and pierce through the bottom wall 51 of the patch body 5 and the skin of the human body. As shown in FIGS. 11C and 12C, when the torsion spring 336 is continuously rotated, the movable seat 334 is pulled back to its original position through the action of the pivot arm assembly 335, and retracts the guide needle 332 leaving the sensor 31 implanted in the skin of the human body. The conductive members 32 can clamp the sensor 31 through its own resiliency to electrically connect with the same.

To ensure the operation of the trigger mechanism 331, a cover body 338 (see FIGS. 12A to 12C) can be further provided for covering the insertion device 33 and prevent the elastic body from flowing into the trigger mechanism 331, which may cause its damaged, during the making of the patch body 5. The track 333 can be formed on a bottom wall of the cover body 338, as shown in FIG. 12A. Actually, the track 333 is cooperated with the movable seat 334 and can be mounted to any type of substrate.

The elastic physiological patch 100' of the second embodiment not only can achieve the same effect as that of the first embodiment, but also, because the implant assembly 3 is disposed in the chamber 53 of the patch body 5 so that there is no need to cooperate with the external insertion device (see FIG. 8), the implant assembly 3 can be conveniently assembled to the human body. Hence, it is better than the first embodiment.

Figure 13:
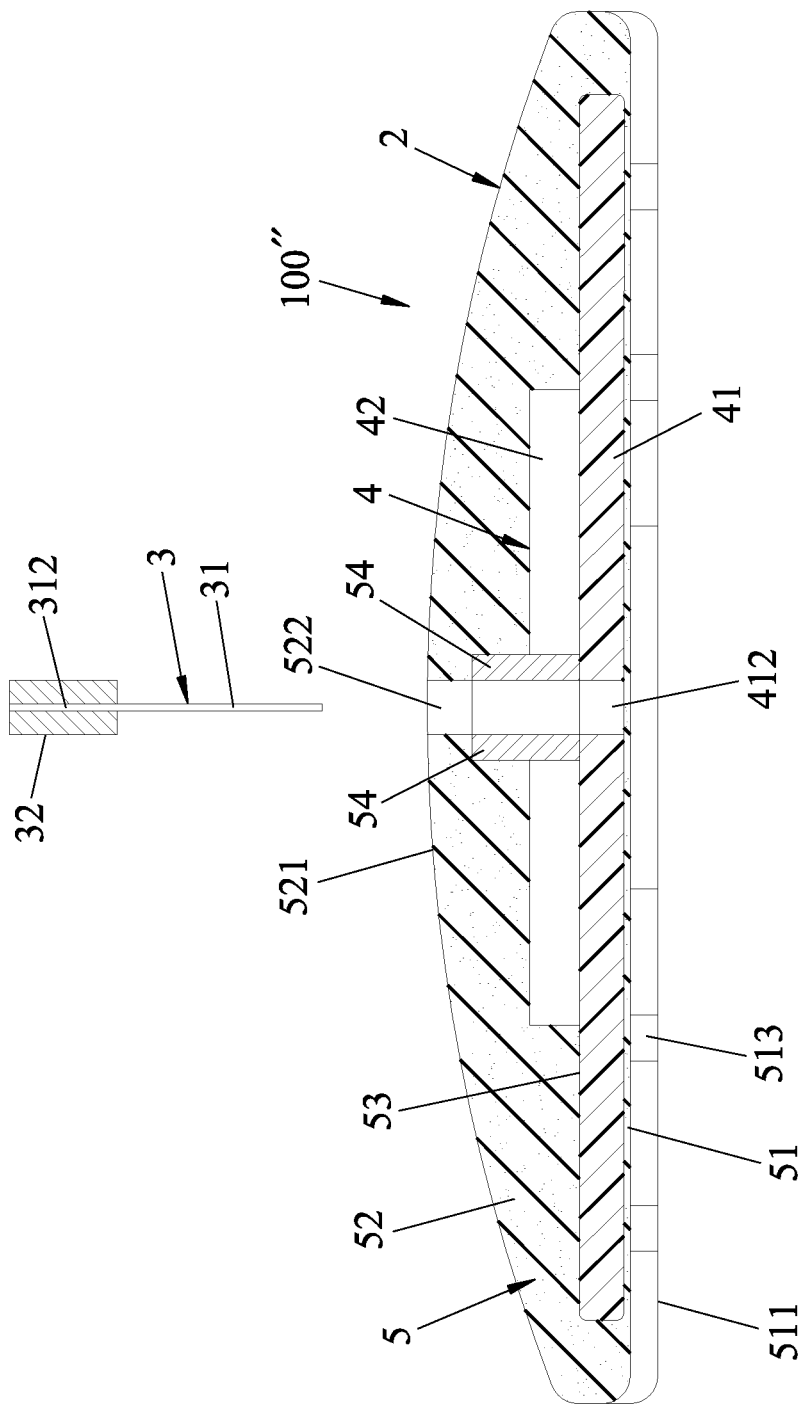
FIG. 13 is a front sectional view of an elastic physiological patch according to the third embodiment of the present disclosure prior to insertion of the implant assembly into the patch assembly.
Figure 14:
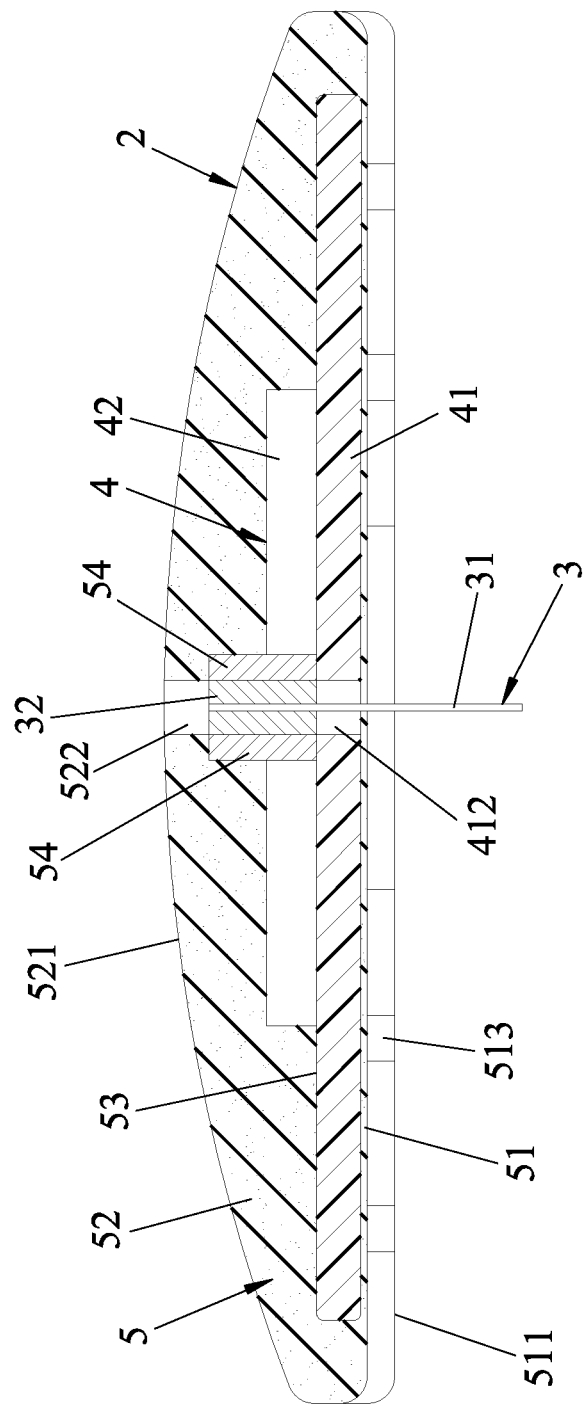
FIG. 14 is a view similar to FIG. 13, but with the implant assembly inserted into the patch assembly.
Figure 15:
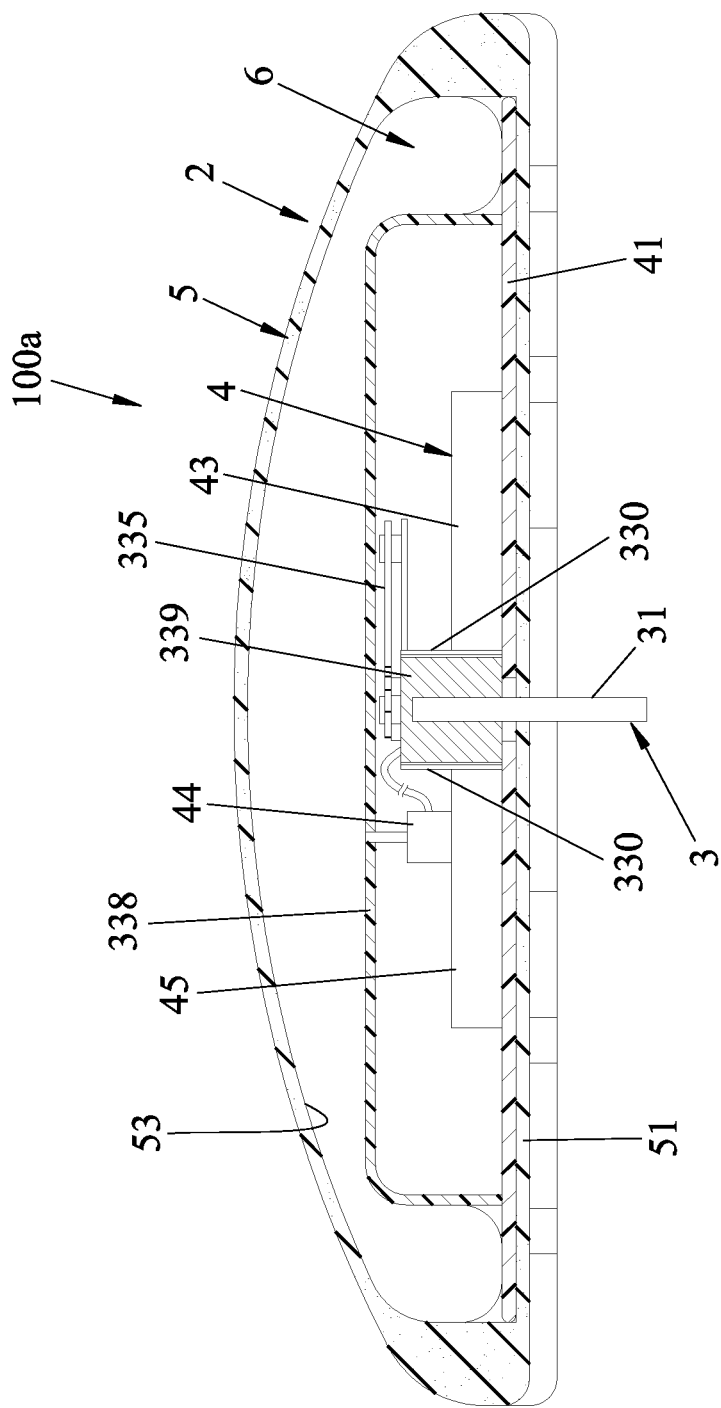
FIG. 15 is a front sectional view of an elastic physiological patch according to the fourth embodiment of the present disclosure.
Figure 16A:
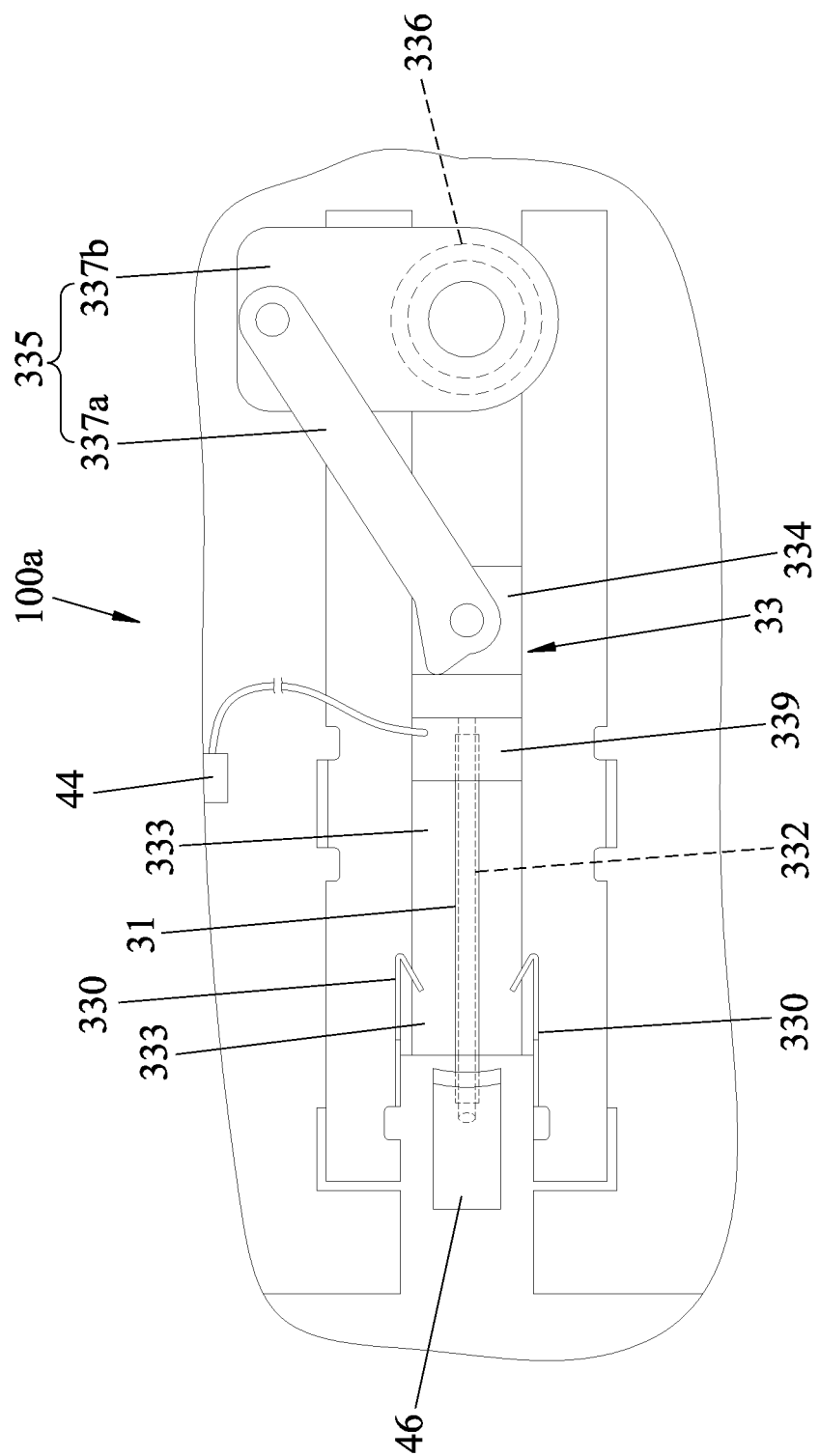
FIG. 16A is a fragmentary top view of the fourth embodiment, illustrating the trigger mechanism prior to being triggered.
Figure 16B:
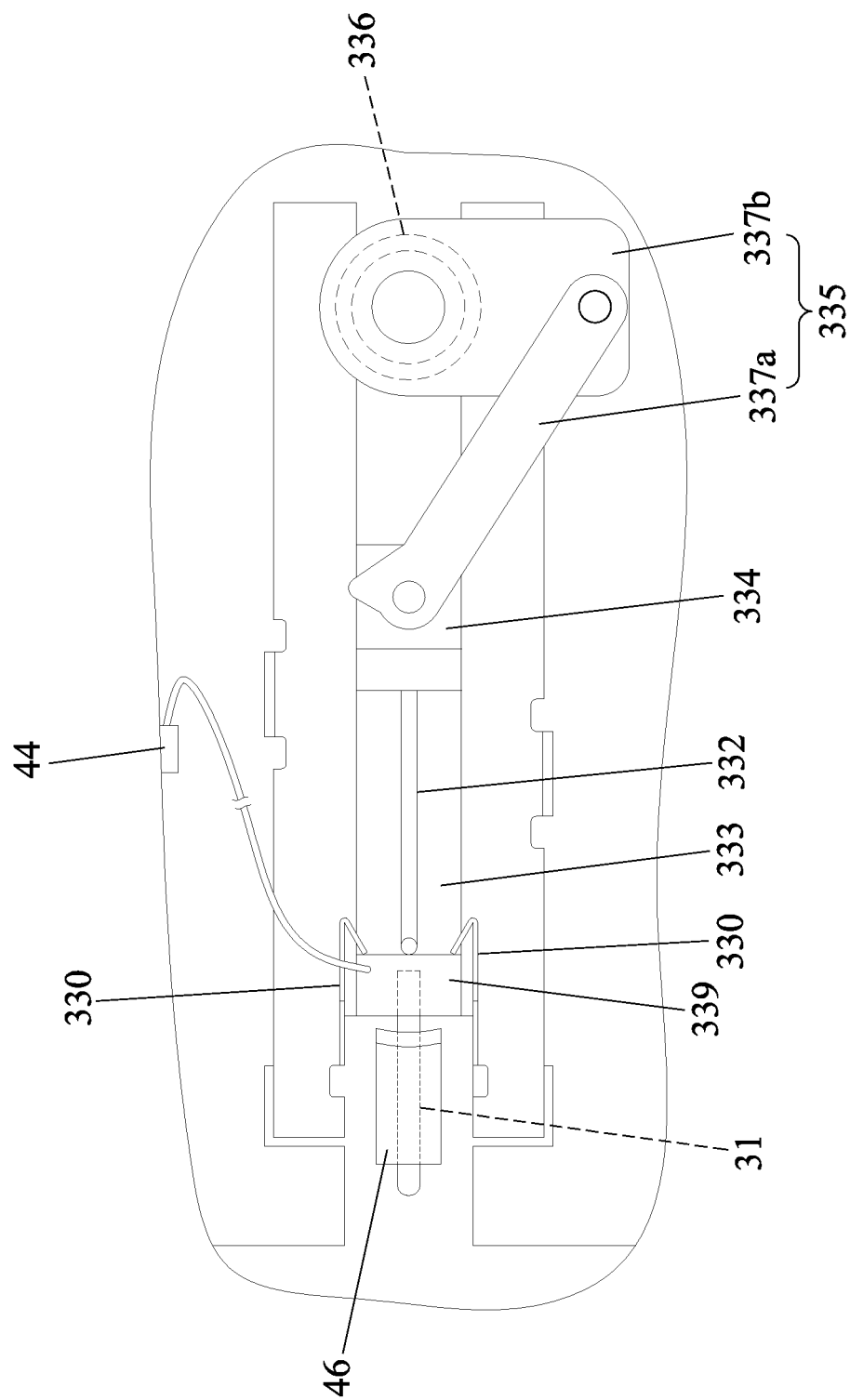
FIG. 16B is a view similar to FIG. 16A, but with the trigger mechanism in a state after being triggered.
Figure 17A:
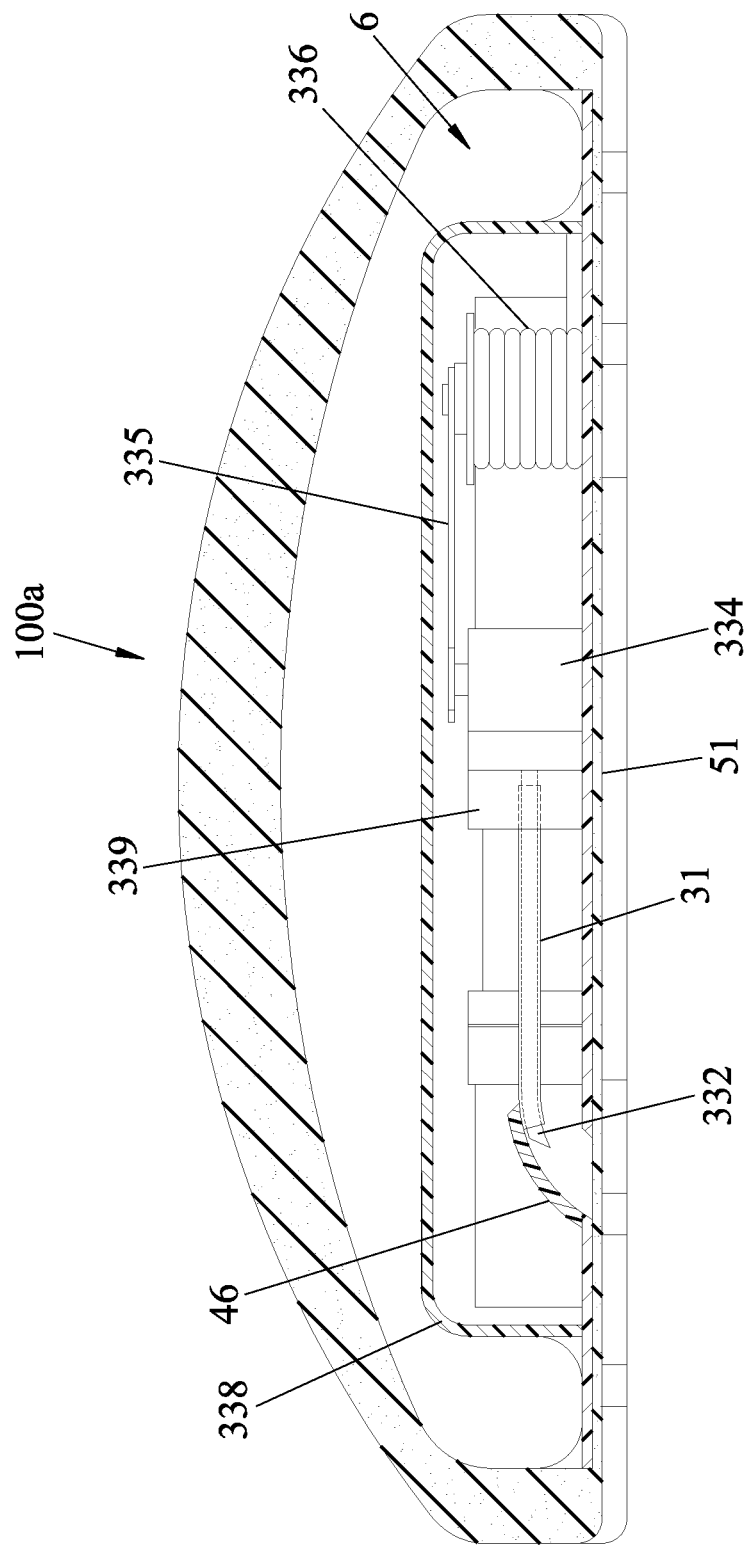
FIG. 17A is a side sectional view of the fourth embodiment, illustrating the trigger mechanism prior to being triggered.
Figure 17B:
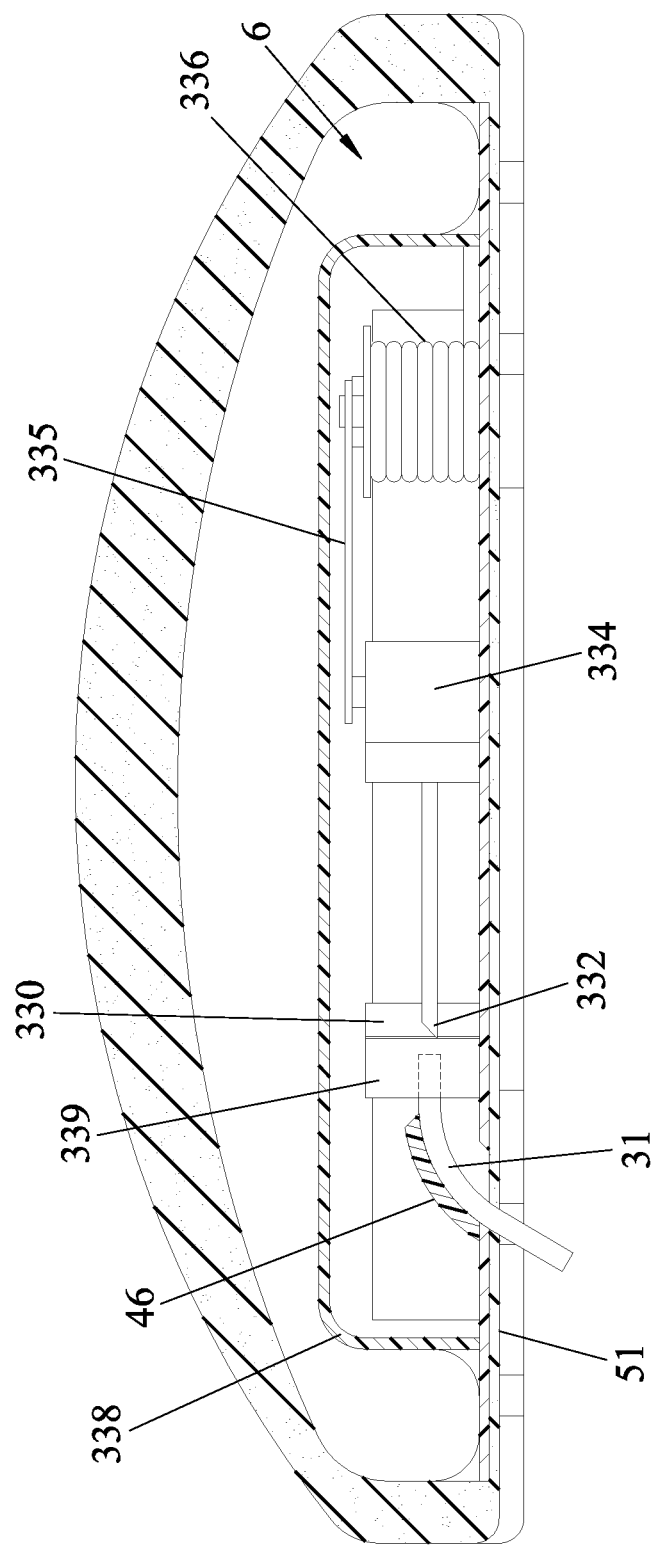
FIG. 17B is a view similar to FIG. 17A, but with the trigger mechanism in the state after being triggered.

Referring to FIGS. 13 and 14, the third embodiment of the elastic physiological patch 100" according to this disclosure is generally identical to the first embodiment, and differs in that, in the third embodiment, the implant assembly 3 further includes a conductive member 32, and the top wall 52 of the patch body 5 has a precut hole 522.

The conductive member 32 is inserted into the signal output end 312 of the sensor 31, and has an outer diameter slightly larger than a diameter of the precut hole 522, so that the conductive member can be pressfitted and embedded in the precut hole 522. Preferably, the outer diameter of the conductive member 32 is larger than the diameter of the precut hole 522 by 0.1 mm to 1 mm.

The depth of the precut hole 522 may be extended down to the through hole 412 in the circuit board 41 so as to communicate with the same, or down to the electrical connection pieces 54 of the patch body 5. After the implant assembly 3 is assembled to the patch body 5, the conductive member 32 is embedded in the precut hole 522, and electrically connects with the electrical connection pieces 54. The mounting of the implant assembly 3 on the patch assembly 2 similarly uses the external insertion device 90 (see FIG. 8) or the guide needle 901 for manual mounting. Since the mounting method is identical to that of the first embodiment, a detailed description thereof is omitted herein for the sake of brevity. Moreover, to enhance the sealing effect of the elastic physiological patch 100", a sealing member (not shown) may be added for sealing the precut hole 522. For example, a sealing member (not shown) may be added and provided on the signal output end 312 of the sensor 31 for contacting or not contacting the conductive member 32. When the implant assembly 3 passes through the precut hole 522 and enters the patch body 5, the conductive member 32 and the sealing member are both embedded in the precut hole 522 to achieve a good sealing effect. However, this disclosure is not limited to the aforesaid example, the sealing member may be added to seal the precut hole 522 after the implant assembly 3 extends into the patch body 5.

Thus, the third embodiment can similarly achieve the same effect as that of the first embodiment. Further, because the patch body 5 is formed with the precut hole 522, during mounting of the implant assembly 3, there is no need for the guide needle 901 to pierce through the top wall 52 of the patch body 5, so that the mounting resistance is small.

Referring to FIGS. 15, 16A, 16B, 17A and 17B, the fourth embodiment of the elastic physiological patch (100a) according to this disclosure is suitable for use in delivering drugs to the human body. In this embodiment, the structure of the patch body 5 is generally identical to that of the second embodiment, but not the structures of the implant assembly 3 and the electronic device 4.

In the fourth embodiment, the implant assembly 3 does not have the conductive members 32 (see FIGS. 11A to 11C), and the implant 31 is a cannula having a tube diameter smaller than 0.5 mm. The insertion device 33 is generally identical to that of the second embodiment, and only differs in that a cannula seat 339 is further provided on the track 333. The implant or cannula 31 is disposed on the cannula seat 339. The guide needle 332 disposed on the movable seat 334 extends through the cannula 31. When the movable seat 334 is released to move along the track 333, the cannula seat 339 will move accordingly. At this time, the guide needle 332 is used to pierce through the bottom wall 51 of the patch body 5 and the skin of the human body. Finally, the movable seat 334 is pulled back to its original position, which in turn retracts the guide needle 332 for leaving the cannula 31 implanted in the skin of the human body. At the same time, the cannula seat 339 is clamped and positioned by two clamping pieces 330 of the insertion device 32 so as to fix the position of the cannula 31.

The electronic device 4 of this embodiment does not include the transmitting unit 42 (see FIG. 4), but includes a liquid drug pump 44, and an electronic control unit 45 for controlling the operation of the liquid drug pump 44. The liquid drug pump 44 is connected to a storage unit 6 disposed in the chamber 53 for delivering liquid drug stored in the storage unit 6 to the cannula 31 and into the human body. In this embodiment, the storage unit 6 is a soft storage bag for storing the liquid drug.

The fourth embodiment similarly has the advantages of convenient use and waterproof effect. Further, the making of the fourth embodiment only needs one time injection of silicone to encapsulate the implant assembly 3, the electronic device 4 and the storage unit 6, so that the manufacturing method thereof is simple.

Figure 18:
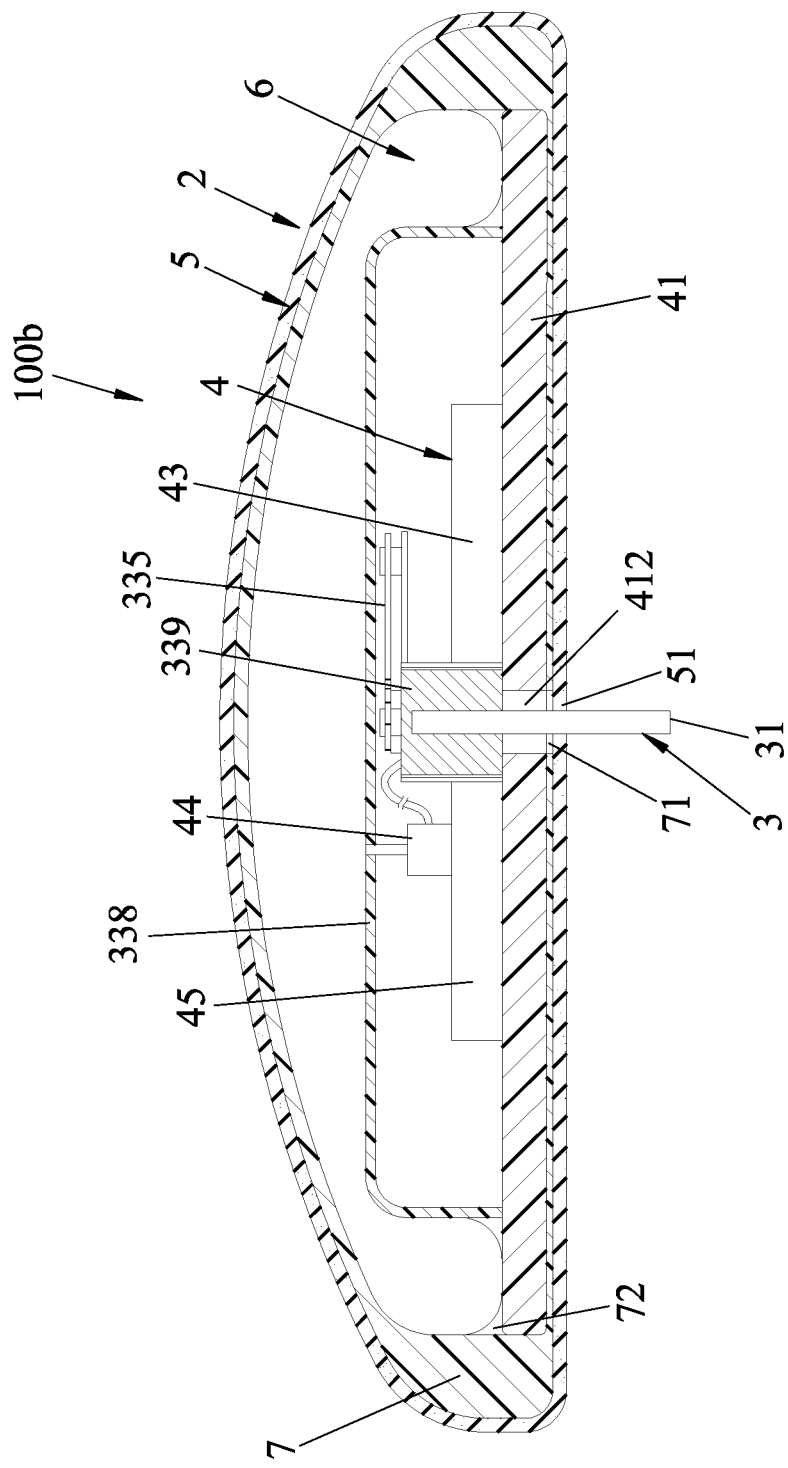
FIG. 18 is a front sectional view of an elastic physiological patch according to the fifth embodiment of the present disclosure.

Referring to FIG. 18, the fifth embodiment of the elastic physiological patch (100b) according to this disclosure is generally identical to the fourth embodiment, and differs in that the patch assembly 2 of the fourth embodiment further includes a hard shell 7. The hard shell 7 is encapsulated by the patch body 5 and is received in the chamber 53. The hard shell 7 defines a receiving space 72 for receiving the implant assembly 3, the electronic device 4, and the storage unit 6, and has an opening 71 for allowing the cannula 31 to pass therethrough.

The material of the hard shell 7 may be selected from the group consisting of acrylonitrile-butadiene-styrene copolymer (ABS), polycarbonate (PC), polypropylene (PE), polyether ether ketone (PEEK), polyterephthalic acid ethylene glycol (PET), polymethyl methacrylate (PMMA), polyoxymethylene (POM), polyvinyl chloride (PVC), chlorinated polyvinyl chloride (CPVC), polytetrafluoroethylene (PTFE), nylon, phenolic resin (PF), glass fiber (FRP), and a combination thereof.

In the making of the fifth embodiment, the hard shell 7 is first made, after which the storage unit 6, the electronic device 4, and the implant assembly 3 are placed in an interior space of the hard shell 7, and then followed by wrapping the elastomer around the hard shell 7 to form the patch body 5.

Thus, the fifth embodiment not only has the effects of the fourth embodiment, in comparison with the conventional hard structure waterproof process, the fifth embodiment only makes changes to the structural design with its outer portion being covered by the soft patch body 5. Hence, this embodiment has a waterproof effect, and the manufacturing process is simple.

Figure 19:
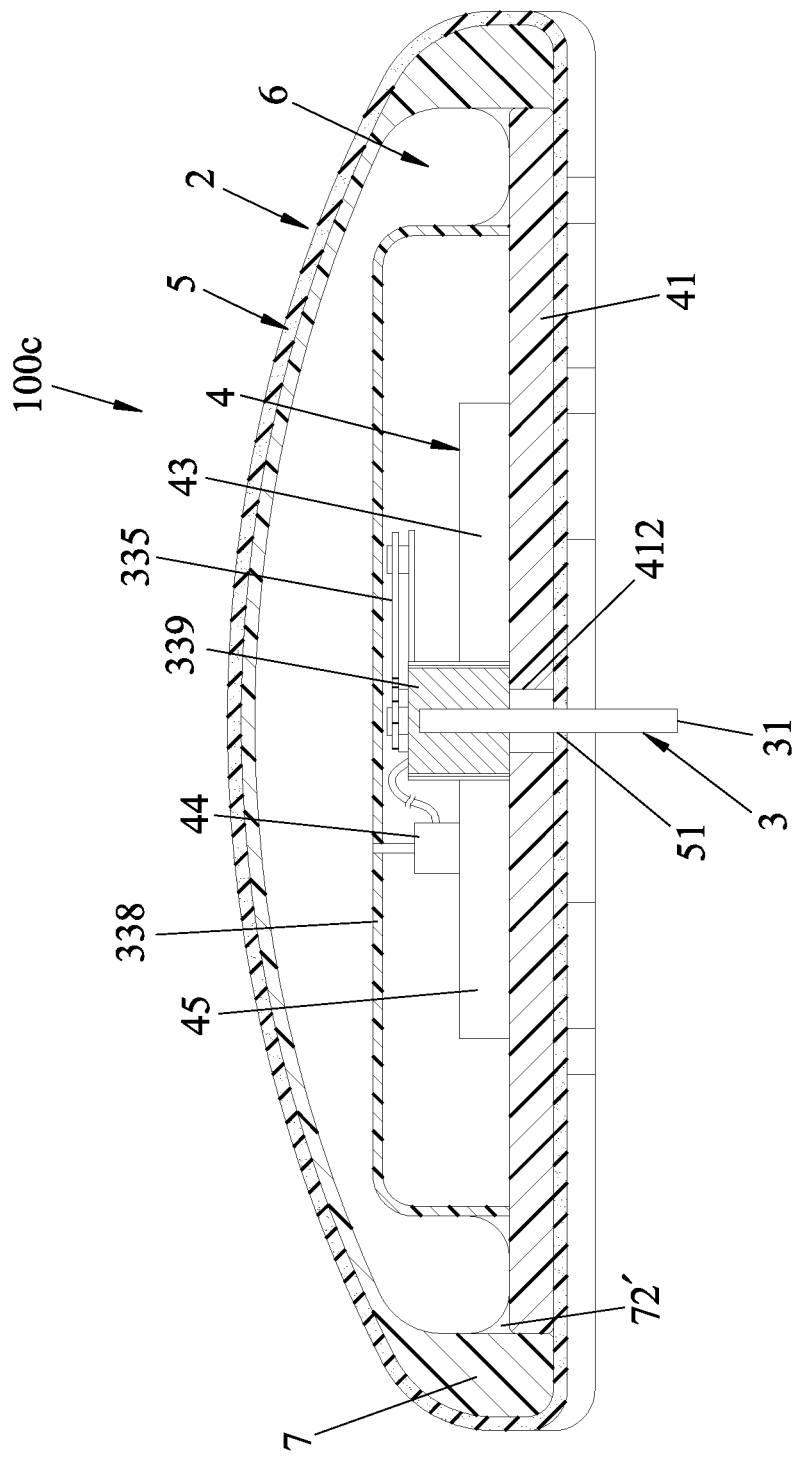
FIG. 19 is a front sectional view of an elastic physiological patch according to the sixth embodiment of the present disclosure.

Referring to FIG. 19, the sixth embodiment of the elastic physiological patch (100c) of the present disclosure is generally identical to the fifth embodiment, and differs in the structure of the hard shell 7. In this embodiment, the hard shell 7 cooperates with the circuit board 41 to define a receiving space 72' for receiving the cannula 31, the storage unit 6 and the other components of the electronic device 4, for example, the liquid drug pump 44, the electronic control unit 45, etc. The sixth embodiment not only has the effects of the fifth embodiment, but also provides another structure of the hard shell 7 for a user to select according to his/her requirement.

In sum, the patch assembly 2 can press tightly against the implant assembly 3 to achieve waterproof and sealing effects, thereby effectively protecting the electronic device 4 in the interior portion thereof. Therefore, the object of this disclosure can indeed be achieved.

In the description above, for the purposes of explanation, numerous specific details have been set forth in order to provide a thorough understanding of the embodiment. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. An elastic physiological patch comprising:
a patch assembly including an electronic device, and a soft patch body that is integrally formed as one piece, that encapsulates said electronic device, and that defines a chamber for receiving said electronic device, said soft patch body having a bottom wall which has an adhering surface for being adhered to the skin of a subject; and
an implant assembly mountable to said electronic device and including an implant;
wherein said implant is capable of being driven to partially pass through said patch body and is adapted to be implanted in the skin of the subject;
wherein said patch body rebounds and tightly holds said implant when said implant is inserted through said patch body, and cooperates with said implant to seal said chamber; and
wherein said patch assembly presses tightly against said implant assembly to achieve waterproof and sealing effects to thereby protect said electronic device in an interior portion of said patch assembly.

2. The elastic physiological patch as claimed in claim 1, wherein said implant assembly is disposed in said chamber and further includes an insertion device having a guide needle, said implant being detachably positioned in said guide needle, said guide needle being operable to guide said implant to pass through said patch body therealong, and being retractable into said chamber for leaving said implant in the skin of the subject.

3. The elastic physiological patch as claimed in claim 1, wherein a guide needle is operable to guide said implant assembly to pass through said patch body from an outer side of said patch assembly, and said implant is detachably disposed in said guide needle.

4. The elastic physiological patch as claimed in claim 1, wherein said electronic device includes a transmitting unit, and said implant is a sensor.

5. The elastic physiological patch as claimed in claim 4, wherein said patch body has two spaced-apart electrical connection pieces for electrically connecting said electronic device to said sensor, each of said electrical connection pieces containing a conductive material.

6. The elastic physiological patch as claimed in claim 4, wherein said patch body has two spaced-apart electrical connection pieces, said sensor having a signal output end, said implant assembly further including a conductive member disposed on said signal output end and electrically connecting with said electrical connection pieces, said conductive member being embedded in said patch body.

7. The elastic physiological patch as claimed in claim 6, wherein said patch body further has a bottom wall, and a top wall opposite to said bottom wall and cooperating with said bottom wall to define therebetween said chamber, said top wall having a precut hole, said conductive member being embedded in said precut hole, said precut hole having a diameter smaller than an outer diameter of said conductive member.

8. The elastic physiological patch as claimed in claim 7, wherein the outer diameter of said conductive member is larger than the diameter of said precut hole by 0.1 mm to 1 mm.

9. The elastic physiological patch as claimed in claim 1, wherein said implant is a cannula, said patch assembly further including a storage unit for storing liquid drug, said electronic device including a liquid drug pump adapted to deliver the liquid drug stored in said storage unit to said cannula.

10. The elastic physiological patch as claimed in claim 9, wherein said patch assembly further includes a hard shell that is encapsulated by said patch body, that is received in said chamber, that defines a receiving space for receiving said storage unit and said electronic device, and that has an opening for allowing said cannula to pass through said hard shell.

11. The elastic physiological patch as claimed in claim 9, wherein said electronic device further includes a circuit board having a through hole for allowing said cannula to pass through said circuit board, said patch assembly further including a hard shell received in said chamber and cooperating with said circuit board to define a receiving space for receiving said cannula, said storage unit and said liquid drug pump.

12. The elastic physiological patch as claimed in claim 9, wherein said electronic device further includes an electronic control unit for controlling the operation of said liquid drug pump.

13. The elastic physiological patch as claimed in claim 1, wherein said patch body has a plurality of long-strip grooves radially formed in said adhering surface.

14. The elastic physiological patch as claimed in claim 1, wherein said patch body is made of an elastomer having an injection temperature ranging from 140 to 170° C.

15. The elastic physiological patch as claimed in claim 14, wherein the elastomer is selected from a group consisting of silica gel, silicone, polyurethane (PU), and a combination thereof.

16. The elastic physiological patch as claimed in claim 1, wherein said patch body has a bottom wall with a thickness ranged from 0.2 mm to 1 mm.

17. An elastic physiological patch comprising:

a patch assembly including an electronic device, and a soft patch body that is integrally formed as one piece, that encapsulates said electronic device, and that defines a chamber for receiving said electronic device, said soft patch body having a bottom wall which has an adhering surface for being adhered to the skin of a subject, and a top wall opposite to said bottom wall and cooperating with said bottom wall to define said chamber; and an implant assembly mountable to said electronic device and including an implant;

wherein said implant is capable of being driven to partially pass through said patch body and is adapted to be implanted in the skin of the subject; and wherein, when said implant is implanted in the skin of the subject, said top wall is free of any opening and said bottom wall of said patch body rebounds and tightly holds said implant and cooperates with said implant to seal said chamber.

18. The elastic physiological patch as claimed in claim 17, wherein said bottom wall has a thickness ranged from 0.2 mm to 1 mm.

19. The elastic physiological patch as claimed in claim 17, wherein said soft patch body encapsulates said electronic device.

20. The elastic physiological patch as claimed in claim 17, wherein said implant assembly is disposed in said chamber and further includes an insertion device having a guide needle, said implant being detachably positioned in said guide needle, said guide needle being operable to guide said implant to pass through said patch body therealong, and being retractable for leaving said implant in the skin of the subject.

* * * * *